US005871724A

United States Patent [19]

Iwata et al.

[11] Patent Number: 5,871,724
[45] Date of Patent: Feb. 16, 1999

[54] TISSUE-DERIVED TUMOR GROWTH INHIBITORS, METHODS OF PREPARATION AND USES THEREOF

[75] Inventors: Kenneth K. Iwata, Westbury; J. Gordon Foulkes, Huntington, both of N.Y.; Peter Ten Dijke, Uppsalla, Sweden; John D. Haley, Great Neck, N.Y.

[73] Assignee: O.S.I. Pharmaceuticals Inc., Uniondale, N.Y.

[21] Appl. No.: 476,014

[22] Filed: Jun. 7, 1995

Related U.S. Application Data

[60] Division of Ser. No. 115,519, Sep. 1, 1993, which is a continuation-in-part of Ser. No. 71,223, Jun. 1, 1993, abandoned, and a continuation-in-part of Ser. No. 543,341, Jun. 25, 1990, Pat. No. 5,262,319, which is a continuation of Ser. No. 543,348, Jun. 25, 1990, abandoned, and a continuation-in-part of Ser. No. 992,479, Dec. 15, 1992, abandoned, which is a continuation-in-part of Ser. No. 948,005, Sep. 21, 1992, abandoned.

[51] Int. Cl.$^6$ ..................................................... A61K 45/05
[52] U.S. Cl. ........................... 424/85.1; 424/85.2; 514/2; 514/12
[58] Field of Search ..................................... 435/335, 325; 424/85.1, 85.2, 145.1; 514/12.2, 21.64; 530/351, 399

[56] References Cited

U.S. PATENT DOCUMENTS

| | | |
|---|---|---|
| 4,863,902 | 9/1989 | Amagase et al. |
| 4,929,442 | 5/1990 | Powell .................................... 424/85.2 |
| 5,199,942 | 4/1993 | Gillis .......................................... 604/4 |
| 5,278,145 | 1/1994 | Keller et al. ............................. 514/12 |

FOREIGN PATENT DOCUMENTS

| | | |
|---|---|---|
| 190018 | 8/1986 | European Pat. Off. |
| 0269408 | 6/1988 | European Pat. Off. |
| 290012 | 11/1988 | European Pat. Off. |
| WO8904664 | 6/1989 | WIPO |
| WO9214480 | 9/1992 | WIPO |
| WO9218153 | 10/1992 | WIPO |

OTHER PUBLICATIONS

Brown et al. (1986) "Enhancement of Epidermal Regeneration By Biosynthetic Epidermal Growth Factor", Journal of Experimental Medicine 163: 1319–1324.

Cheifetz et al. (1987) "The Transforming Growth Factor–β System, a Complex Pattern of Cross–Reactive Ligands and Receptors," Cell 48: 409–415.

Epstein et al. (1988) "The Painful Mouth", Infectious Disease Clinics of North America 2: 183–202.

Gabrilove et al. (1988) "Effect of Granulocyte Colony–Stimulating Factor", New England Journal of Medicine 318: 1414–1422.

Jacobsen et al. (1991) "Bidirectional Effects of Transforming Growth Factor β (TGF–β) on colony–Stimulating Factor–Induced Human Myelopoiesis In Vitro: Differential Effects of Distinct TGF–β Isoforms," Blood 78(9): 2239–2247.

Konturek et al. (1981) "Gastric Cytoprotection by Epidermal Growth Factor," Gastroenterology 81: 483–443.

Lawrence et al. (1984) "Reversal of an Adriamycin Induced Healing Impairment with Chemoattractants and Growth Factors," Ann. Surg 203:142–147.

Niall et al. (1982) "The Effect of Epidermal Growth Factor on Wound Healing in Mice," Journal of Surgical Research 33: 164–169.

Peterson et al. (1982) "Oral Complications of Cancer Chemotherapy: Present Status and Future Studies", Cancer Treatment Reports 66: 1251–1256.

Robinson et al. (1985) "Epidermal Growth Factor (hEGF) Has No Effect on Murine Intestine Epithelial Damage and Regeneration After Melphalan", Br. J. Cancer 52: 733–737.

Rosa et al. (1988) "Mesoderm Induction in Amphibians: The Role of TGF–β2–Like Factors," Science 239: 783–785.

Sonis et al. (1990) "An Animal Model for Mucositis Induced by Cancer Therapy", Oral Surg. Oral Med. Oral Pathol. 69: 437–443.

Sonis et al. (1992) "Effect of Epidermal Growth Factor on Ulcerative Muscositis in Hamsters that Receive Cancer Chemotherapy", Oral Surg. Oral Med. Oral Pathol. 74: 749–755.

Southgate et al. (1987) "Primary Culture of Human Oral Epithelial Cells", Laboratory Investigation 56: 211–223.

Steidler et al. (1980) "Histomorphological Effects of Epidermal Growth Factor on Skin and Oral Mucosa in Neonatal Mice", Archives of Oral Biology 25: 37–43.

Takehara, K. et al. (1987) "TGF–β Inhibition of Endothelial Cell Proliferation: Alteration of EGF Binding and EGF–Induced Growth–Regulatory (Competence) Gene Expression", Cell 49:415–422.

Roberts et al., PNAS, vol. 82, pp. 119–123, Jan. 1985.

Miller et al., NY Acad. Sci. 0(0) pp. 208–217 1990, Conference on the Betas In 1989.

*Primary Examiner*—Laurie Scheiner
*Attorney, Agent, or Firm*—John P. White; Cooper & Dunham LLP

[57] ABSTRACT

The present invention provides a method for inhibiting cytotoxic poisoning of normal cells in a subject which comprises administering to the subject an amount of a Transforming Growth Factor Beta effective to slow the growth of normal cells and thereby inhibit the cytotoxic poisoning of the normal cells in the subject. Typically, administration is topical and initiated prior to anti-neoplastic therapy such as radiation treatment or chemotherapy. The invention is particularly suited for pediatric patients.

32 Claims, 21 Drawing Sheets

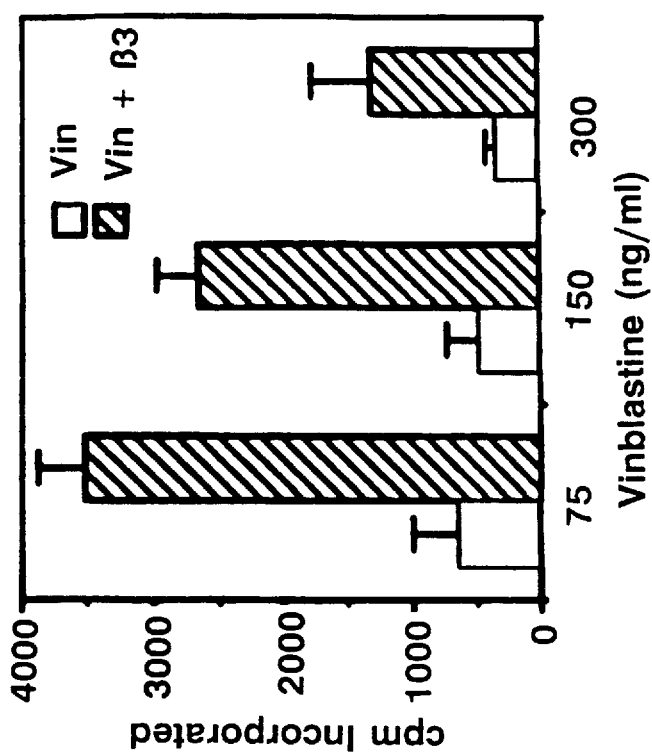
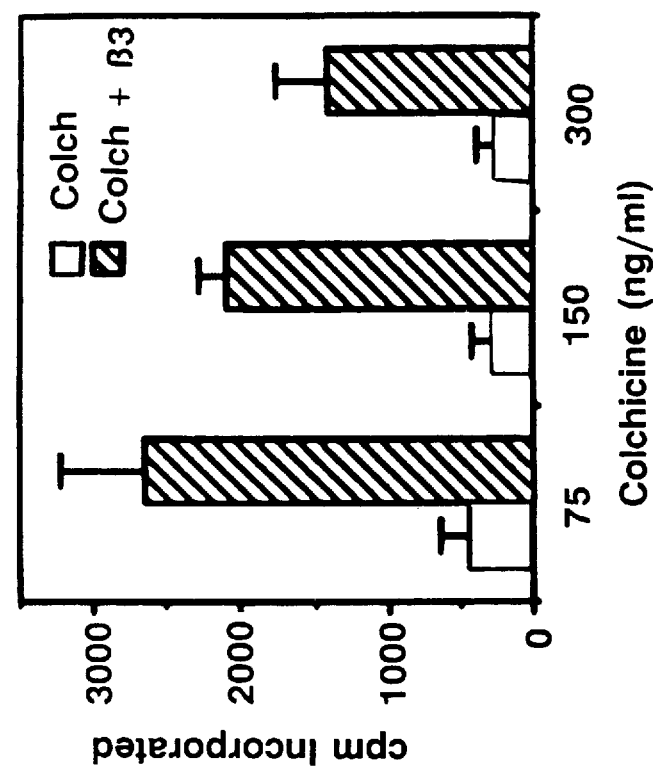
FIG. 1A
FIG. 1B

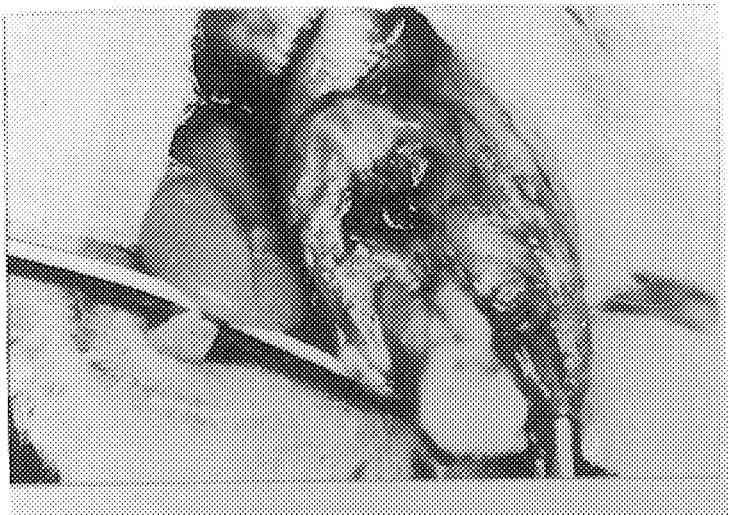
FIG. 2A Group 1
FIG. 2B Group 2
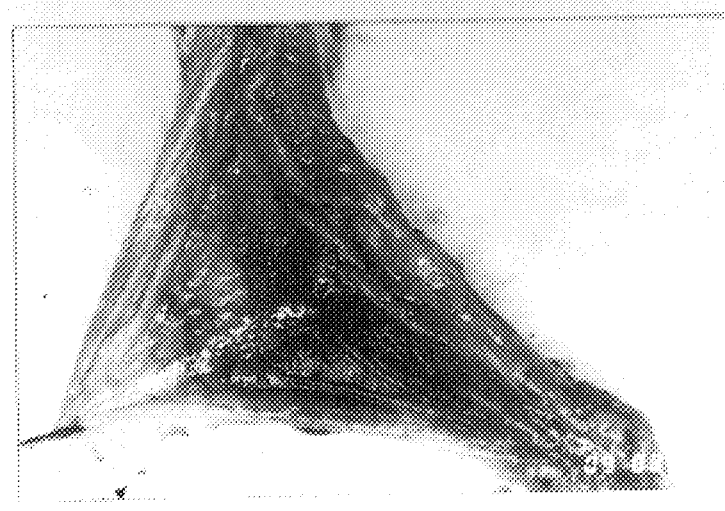
FIG. 2C Group 3

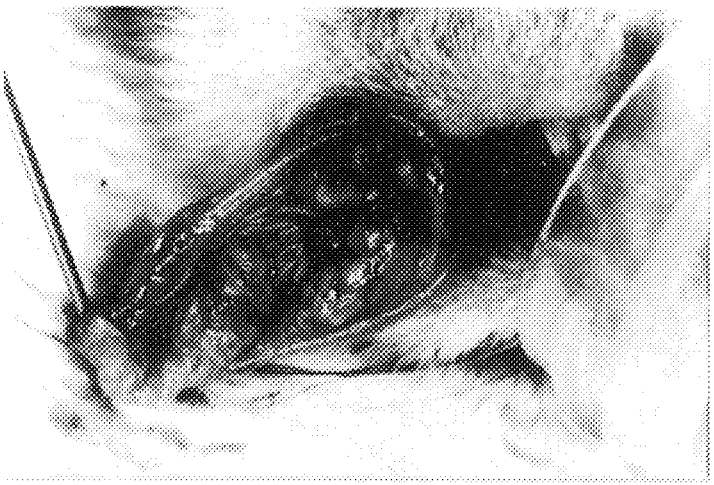
FIG. 2D Group 1
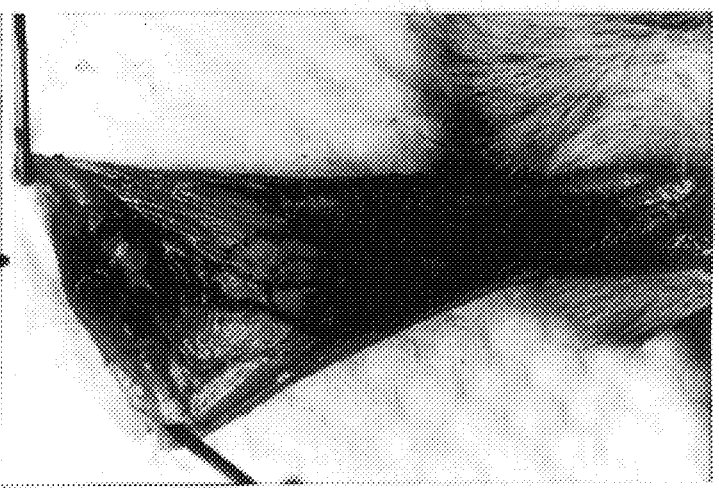
FIG. 2E Group 2
FIG. 2F Group 3

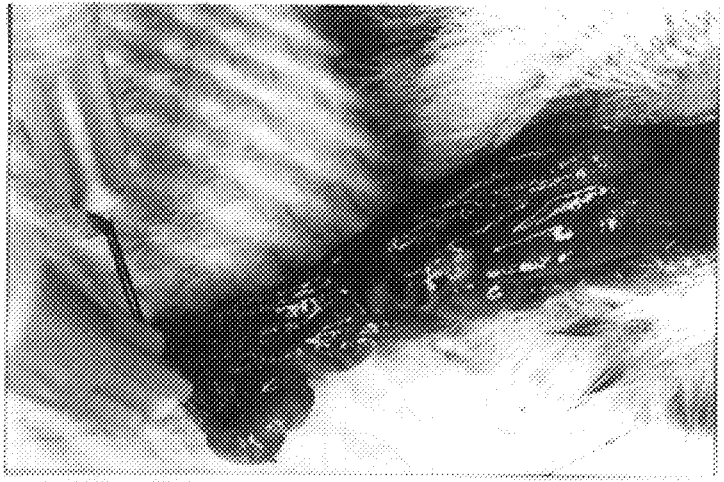
FIG. 2G Group 1
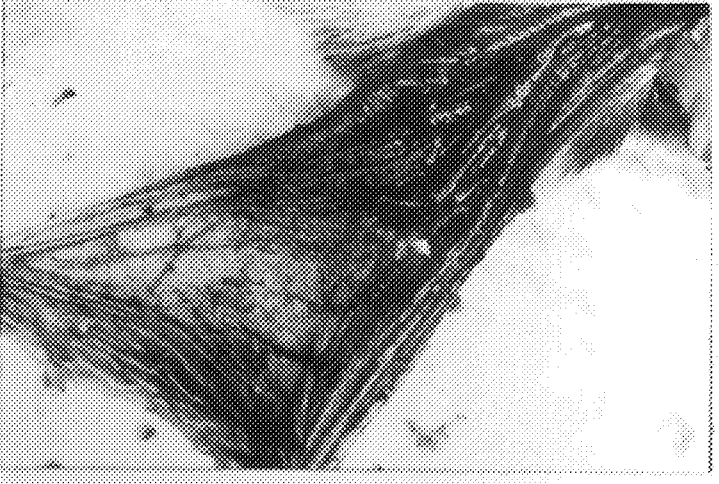
FIG. 2H Group 2
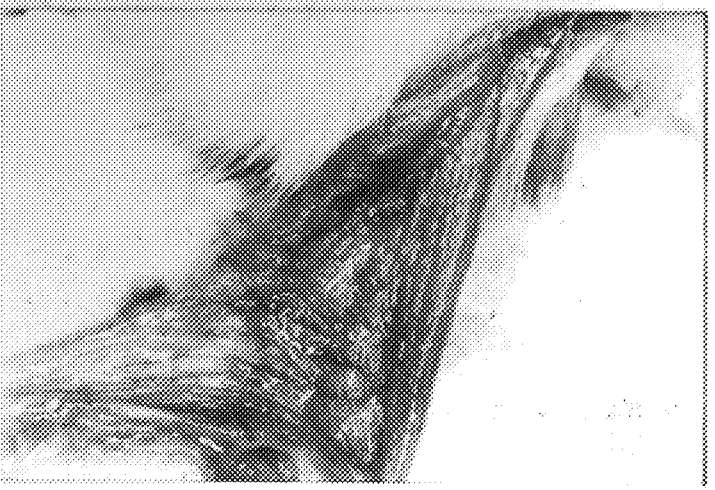
FIG. 2I Group 3

With TGF-β3 Treatment

Duodenum

With TGF-β3 Treatment

Jejunum

Without TGF-β3 Treatment

Duodenum

Without TGF-β3 Treatment

Jejunum

With TGF-β3 Treatment
Duodenum

With TGF-β3 Treatment
Jejunum

With TGF-β3 Treatment
Ileum

Without TGF-β3 Treatment

Duodenum

Without TGF-β3 Treatment

Jejunum

Without TGF-β3 Treatment

Ileum

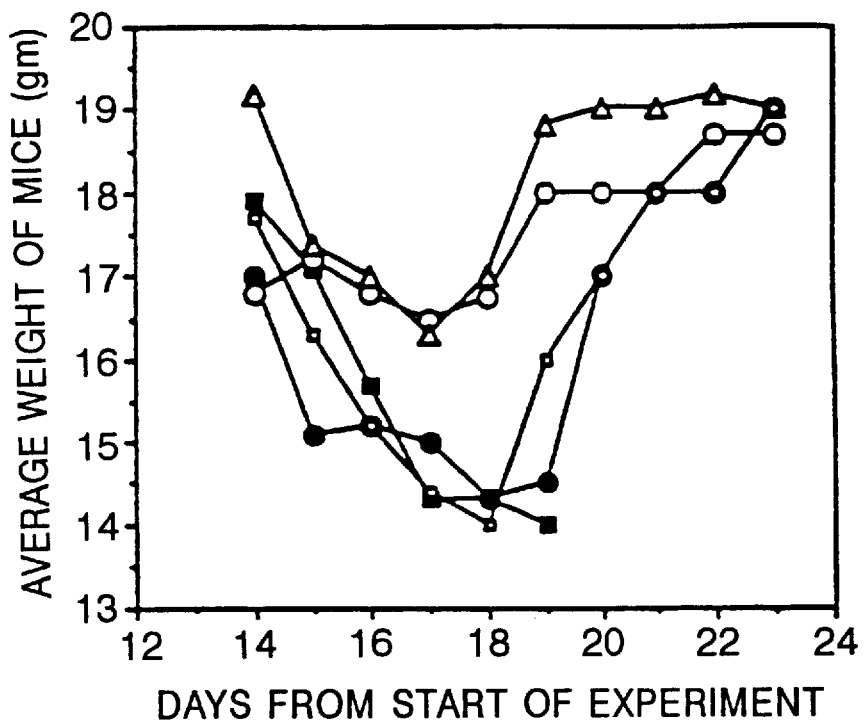
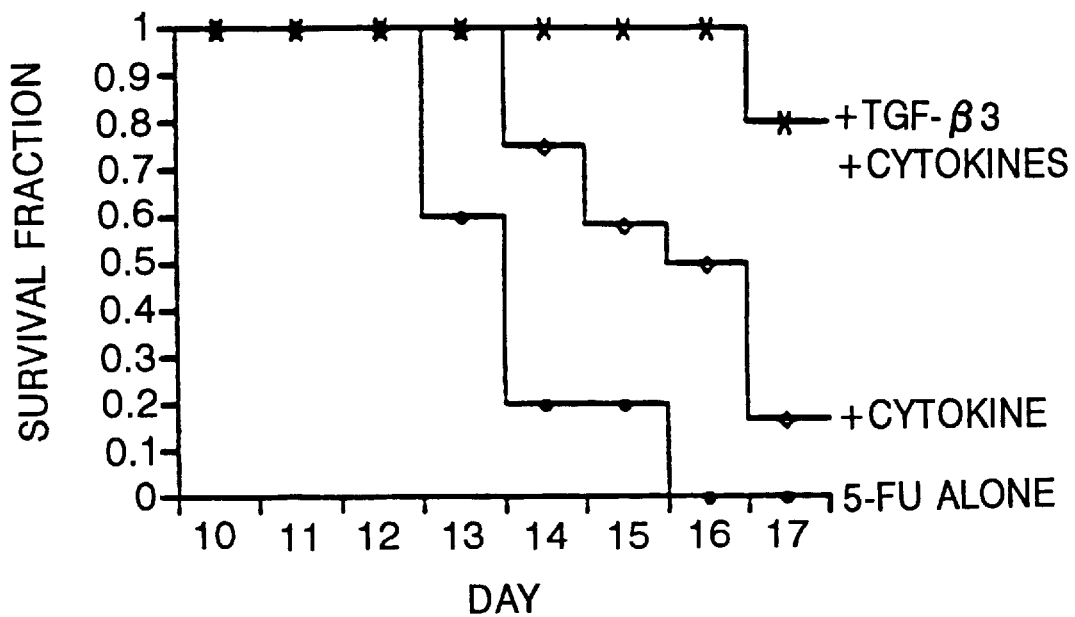

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg  Lys  Lys  Arg
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Ile  Glu  Gly  Arg
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Pro  Xaa  Gly  Pro
    1

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

His  Xaa  Xaa  Xaa  Trp
    1                        5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Gly  Asp  Asp  Asp  Lys
    1                        5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Ile  Val  Gly  Gly  Thr  Val
    1                        5

( 2 ) INFORMATION FOR SEQ ID NO:7:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Pro  Phe  Arg
    1

( 2 ) INFORMATION FOR SEQ ID NO:8:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Gly  Pro  Arg
    1

TISSUE-DERIVED TUMOR GROWTH INHIBITORS, METHODS OF PREPARATION AND USES THEREOF

This application is a divisional of U.S. Ser. No. 08/115, 519, filed Sept. 1, 1993, which is continuation-in-part of U.S. Ser. No. 543,341, filed Jun. 25, 1990, now U.S. Pat. No. 5,262,319, and U.S. Ser. No. 08/071,223, filed Jun. 1, 1993, now abandoned, which is a continuation of 07/543,348, filed on Jun. 25, 1990, now abandoned. This application is also a continuation-in-part of U.S. Ser. No. 07/992,479, filed Dec. 15, 1992, now abandoned, which is a continuation-in-part of U.S. Ser. No. 07/948,005, filed Sept. 21, 1992, now abandoned.

Throughout this application, various publications are referenced by author and date in parentheses. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Currently, 800,000 patients receive chemotherapy in the United States each year. Myelosuppression and mucositis are common major side effects in conventional chemotherapy and are exacerbated by high dose and/or schedule intensification. As chemotherapeutic dosage has been identified as a major predictor of treatment outcome in a variety of cancer treatment programs, overcoming dose limiting toxicity has become a major goal for oncologists. Thus, to allow intensification of chemotherapy, it will be essential to prevent these unwanted side effects.

Studies have shown that both oral and gastrointestinal toxicity are a major problem in the clinic (Guggenheimer et al., 1977; Lockhart et al., 1981; Sonis et al., 1988; and Sonis & Clark, 1991). This toxicity is very common and has become dose or schedule limiting in both standard and high dose chemotherapy. As improvements are made in management of hematopoietic toxicity, oral toxicity is more frequently dose and schedule limiting. For example, 67% of leukemia/lymphoma patients, 75% of patients receiving bone marrow transplants following therapy, and approximately 20% of breast cancer patients, suffer from oral mucositis. It has been estimated that 40% of chemotherapy patients develop oral complications (Sonis et al., 1978). Many colon cancer patients receiving 5-fluorouracil (5-FU) suffer from oral mucositis.

Chemotherapy agents which cause oral and gastrointestinal mucositis include commonly prescribed agents. Single-agent or combination therapies which result in dose or schedule limiting oral and gastrointestinal (GI) toxicity include, but are not limited to, 5-FU, methotrexate, doxorubicin, Melphalan (see also Table A), and regimens such as the AFM regimen, the CEA regimen and the CAF regimen (Sonis et al., 1990). Cytotoxic agents, such as antiviral agents, also cause mucositis.

Oral mucositis following chemotherapy is a consequence of the high proliferative rate of the normal epithelial cells lining the oral cavity. Chemotherapy-induced mucositis in the oral cavity is largely derived from injury to the basal epithelial cell layer. The epithelial lining of the mouth is generally five cells thick, with the self-renewing stem cell layer located at the base, which itself overlays a fibrous connective tissue matrix. In contrast to skin, most of the epithelium which lines the oral cavity is not highly keratinized, and therefore is able to absorb and elicit a biological response to exogenously added peptide growth factors. The epithelium at the base of the mouth divides most rapidly and is most sensitive to chemotherapy.

The extent of oral mucositis appears dependent on the cycling status of the epithelial cell layer. For example, 90% of pediatric chemotherapy patients (ages 1–20) develop oral mucositis, as compared with 18% of patients over the age of sixty (Sonis et al., 1979). Further, in animal models of oral mucositis, increasing proliferation of the oral epithelium by prior administration of most growth factor (e.g. EGF, TGF-$\alpha$) markedly increases the severity of oral mucositis. These positively acting factors are currently being evaluated for wound healing.

Oral mucositis leads to epithelial thinning and ulceration resulting in severe pain, weight loss from failure to eat or drink (often requiring parenteral feeding), infection (bacterial, fungal and viral), fever, nausea and diarrhea. Symptoms peak 7 to 10 days following therapy, and gradually recede over the following two weeks. Another major complication is potentially life-threatening infection due to sepsis. Therefore, methods of preventing oral toxicity would enable escalated schedules and doses of a chemotherapy regimen, resulting in improved patient long term survival for many human cancers, notably breast, lung and testicular cancer, leukemia, lymphoma, and neuroblastoma.

Chemotherapy-induced mucositis in the intestinal tract (gastrointestinal mucositis) is also marked and often dose limiting. In the development of the intestinal crypt, primitive stem cells in the proliferative zone at the base of the crypt give rise to more differentiated cell progeny which rapidly migrate to the top of the crypt. These more highly differentiated transitional cells have increasingly less capacity for self renewal and are eventually sloughed off at the top of the crypt. Cell proliferation is restricted to a centrally located band of cells (about ten cell layers deep) within the crypts. Within this band the cells divide rapidly (every ten to fourteen hours) and the product of this division activity matures and moves out of the crypt, onto the villus and is eventually lost within two to three days from the villus tip. Damage to the GI tract increases the risk of sepsis. Thus, like oral mucositis, there is a need to prevent gastrointestinal toxicity. TGF-$\beta$ is part of a family of multifunctional proteins which modulate, alone or in combination with other molecules, cell proliferation and differentiation. Mature TGF-$\beta$ is produced from a precursor form, consisting of a pro-region and mature TGF-$\beta$. Known isoforms of mature TGF-$\beta$ are designated TGF-$\beta$1, TGF-$\beta$2, TGF-$\beta$3, TGF-$\beta$4, and TGF-$\beta$5 (Brunner 1988). Mature TGF-$\beta$ has been isolated from various species (See EP 105,211 and U.S. Pat. No. 5,104,977). Across species TGF-$\beta$s e.g. murine, bovine, human, and porcine show very little difference in amino acid composition. The expression of TGF-$\beta$ in both normal and transformed cells, and methods of producing biologically active mature TGF-$\beta$ from eucaryotic cells have been described (Madisen et al., 1988, Pincher et al., 1985, Assoian et al., 1983, Wrann et al., 1987).

TGF-$\alpha$ and TGF-$\beta$ are not homologous structures at the protein level and do not exhibit any sequence conservation at the nucleic acid level. As shown in Table 1 below, their physical and biological properties are also different.

TABLE 1

COMPARISON OF PROPERTIES OF TGF-α and TGF-β

|  | TGF-α | TGF-β |
|---|---|---|
| Physical Properties: | | |
| Quaternary structure | monomer | dimer |
| Subunit (amino acids) | 50 | 112 |
| Biological Properties: | | |
| EGF receptor-binding | + | − |
| Mitogenic activity in epithelial cells | + | − |
| Arrests cell cycle in epithelial cells | − | + |
| Stimulates fetal bone and collagen production | − | + |

The ability of growth factors to accelerate healing is well known. Recently, Florine et al. U.S. Pat. No. 5,102,870, issued Apr. 7, 1992, described the use of positively acting growth factors and combinations to aid in the healing of oral mucositis. In contrast, TGF-β is a negative regulator of epithelial cell division.

Myelosuppression has been a major dose-limiting toxicity in cancer chemotherapy, and antiviral therapy, e.g. AZT in AIDS therapy or management, which derives from the high proliferative rate of the hematopoietic compartment. The bone marrow contains a totipotent stem cell population that can give rise to a wide variety of cell types involved in oxygen transport, defense against infection. Granulocyte and neutrophil progenitor cells proliferate rapidly and their mature counterparts live only one to two days in the circulation. Consequently, 10–14 days after initiation of chemotherapy, the granulocyte and neutrophil population fall rapidly to a nadir. A reduction in megakaryocyte and erythroid precursor cell populations are also observed but this is less pronounced due to the longer life of their differentiated progeny. Thus, in many of the conventional protocols, chemotherapy is scheduled to maximize granulocyte/neutrophil recovery and to minimize infection.

Recent animal model data suggest that the ability to reconstitute the mature blood cell types decreases progressively with multiple rounds of chemotherapy, and administration of either G-CSF or GM-CSF accelerates the loss of self renewal capacity (Hornung and Longo, 1992). This phenomenon appears to result from progressive damage to the hematopoietic stem cell population. Although stem cells are normally quiescent, they are induced into active division following the first round of chemotherapy and thus become highly susceptible to the subsequent administration of cytotoxic drugs. Extensive experimentation has clearly demonstrated the phenomenon of stem cell depletion following multiple rounds of chemotherapy in animal models. This loss of hematopoietic renewal was one of the major driving forces behind the development of autologous bone marrow transplantation.

Amento et al. U.S. Pat. No. 5,108,989 issued April 28, 1992 discloses the systemic use of TGF-β for predisposition of mammals to accelerated tissue repair. In contrast the present invention involves a method for inhibiting the cytotoxic poisoning of normal cells by slowing their growth.

SUMMARY OF THE INVENTION

The present invention provides a method for inhibiting cytotoxic poisoning of normal cells in a subject which comprises administering to the subject an amount of a Transforming Growth Factor Beta effective to slow the growth of normal cells and thereby inhibit the cytotoxic poisoning of the normal cells in the subject. Typically, administration is topical and initiated prior to anti-neoplastic therapy such as radiation treatment or chemotherapy. The invention is particularly suited for pediatric patients.

BRIEF DESCRIPTION OF THE FIGURES

FIGS. 1A and 1B: Evaluation of TGF-β3 as an chemoprotective agent of epithelial cells in vitro, challenging mink cells with colchicine and vinblastine.

FIGS. 2A–2I: Hamster cheek pouches on FIGS. 2A–2C day 9; FIGS. 2B–2F day 11; and FIGS. 2G–2J day 13 post primary treatment with 5-FU, with placebo treatment (Group 1), 2 µg TGF-β3 topical treatment (Group 2), or 20 µg TGF-β3 topical treatment (Group 3).

FIGS. 10A–10D show BDF mice four days following second 5-FU injection with and without TGF-β3. FIGS. 11A–11F show Balb/c mice four days after second 5-FU injection.

FIGS. 12A–12C: FIG. 12A and 12C show enhanced survival of 5-FU treated mice by TGF-β3 with cytokines G-CSF and IL-1 (-●- 5-FU alone; -◊- 5-FU and cytokines; -x- 5-FU and cytokines and TGF-β3). FIG. 12B shows enhanced weight retention of TGF-β3 treated mice undergoing 5-FU chemotherapy (-●- control; -■- cytokines; -o- 3× TGF-β3 2 µg with cytokines; -Δ- 4× TGF-β3 2 µg with cytokines; -□- 6× TGF-β3 2 µg with cytokines).

FIG. 14 shows a theoretical plot of TGF-$\beta$3 chemoprotection from high dose chemotherapy (—chemotherapy only; —chemotherapy+TGF-$\beta$3).

DETAILED DESCRIPTION OF THE INVENTION

Figure 3:
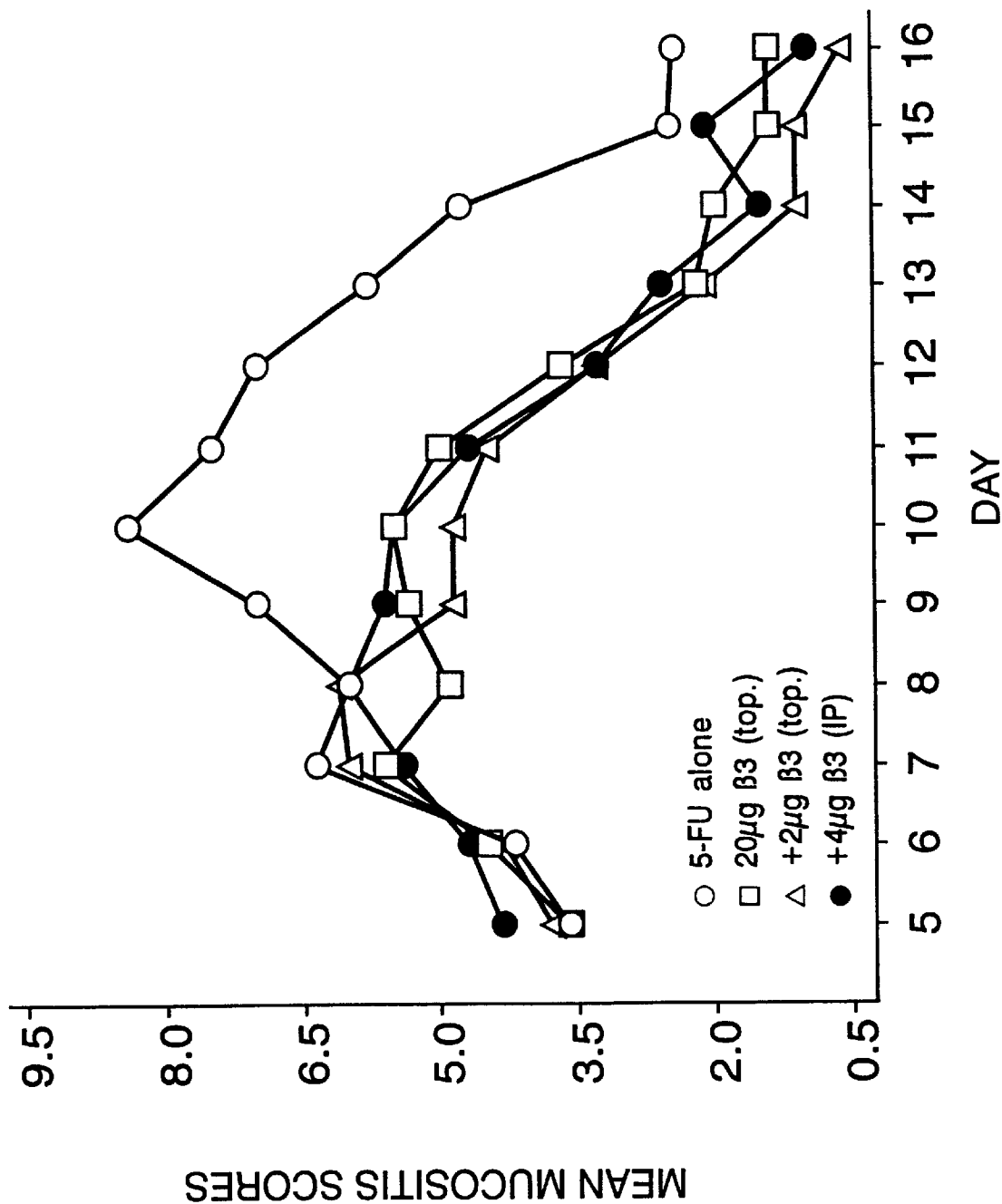
FIG. 3: Mean mucositis scores on days 5 through 16 of hamsters treated i.p. with 5-FU on days 0 and 2 at doses of 60 mg/kg and 40 mg/kg respectively. Group 1: (Open circles) treatment with 5-FU alone. Group 2: (Open triangles) treatment with 5-FU and 2 µg TGF-β3 topically. Group 3: (Open squares) treatment with 5-FU and 20 µg TGF-β3 topically. Group 6 (Filled circles) treatment with 5-FU and 4 µg TGF-β3 intraperitoneally.
Figure 4:
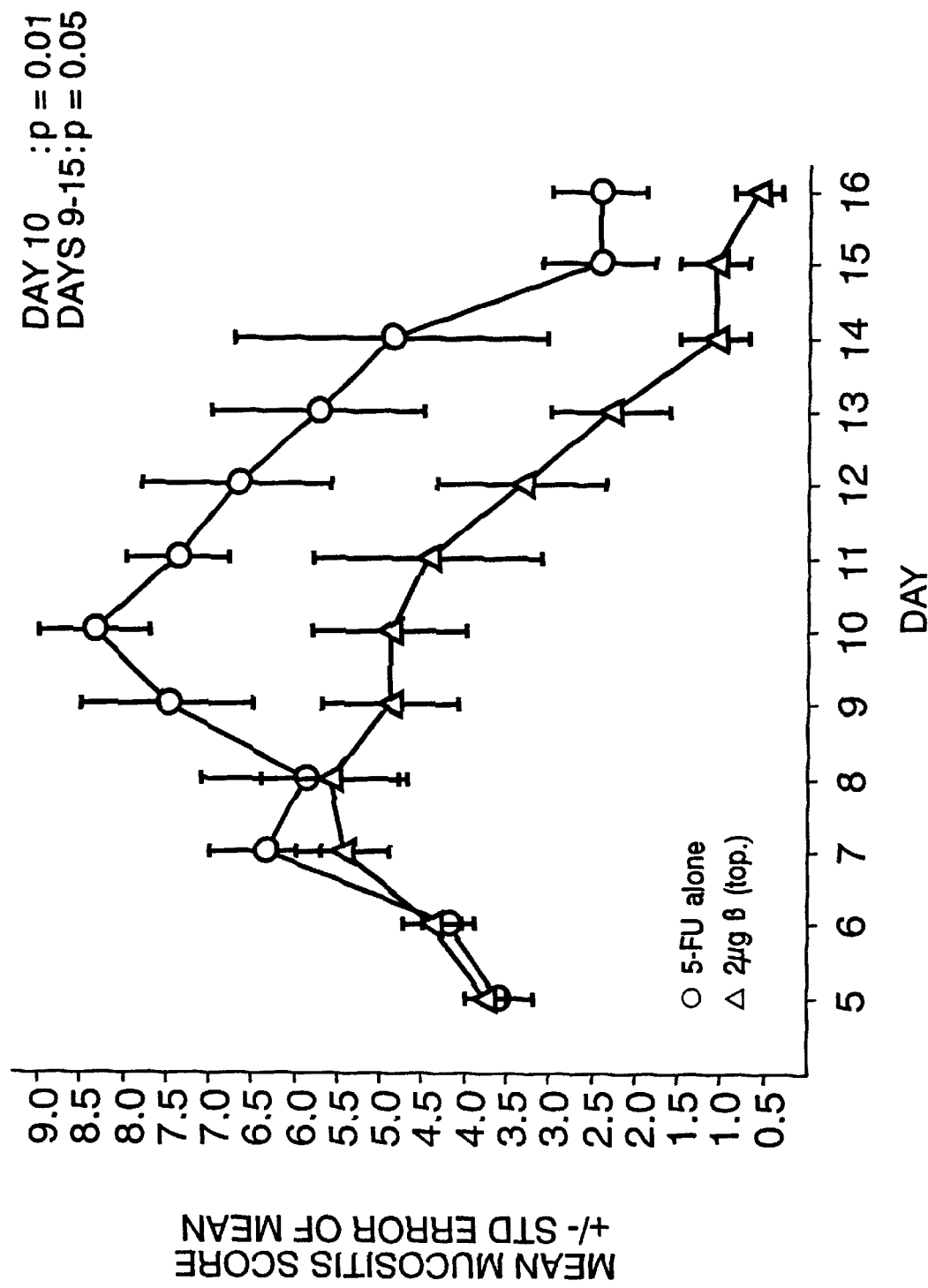
FIG. 4: Statistical significance data for Group 2: (Open circles) treated with 5-FU alone. Group 2: (Open triangles) 5-FU with 2µg TGF-β3 topically. Error bars represent the standard error about the mean mucositis score.
Figure 5:
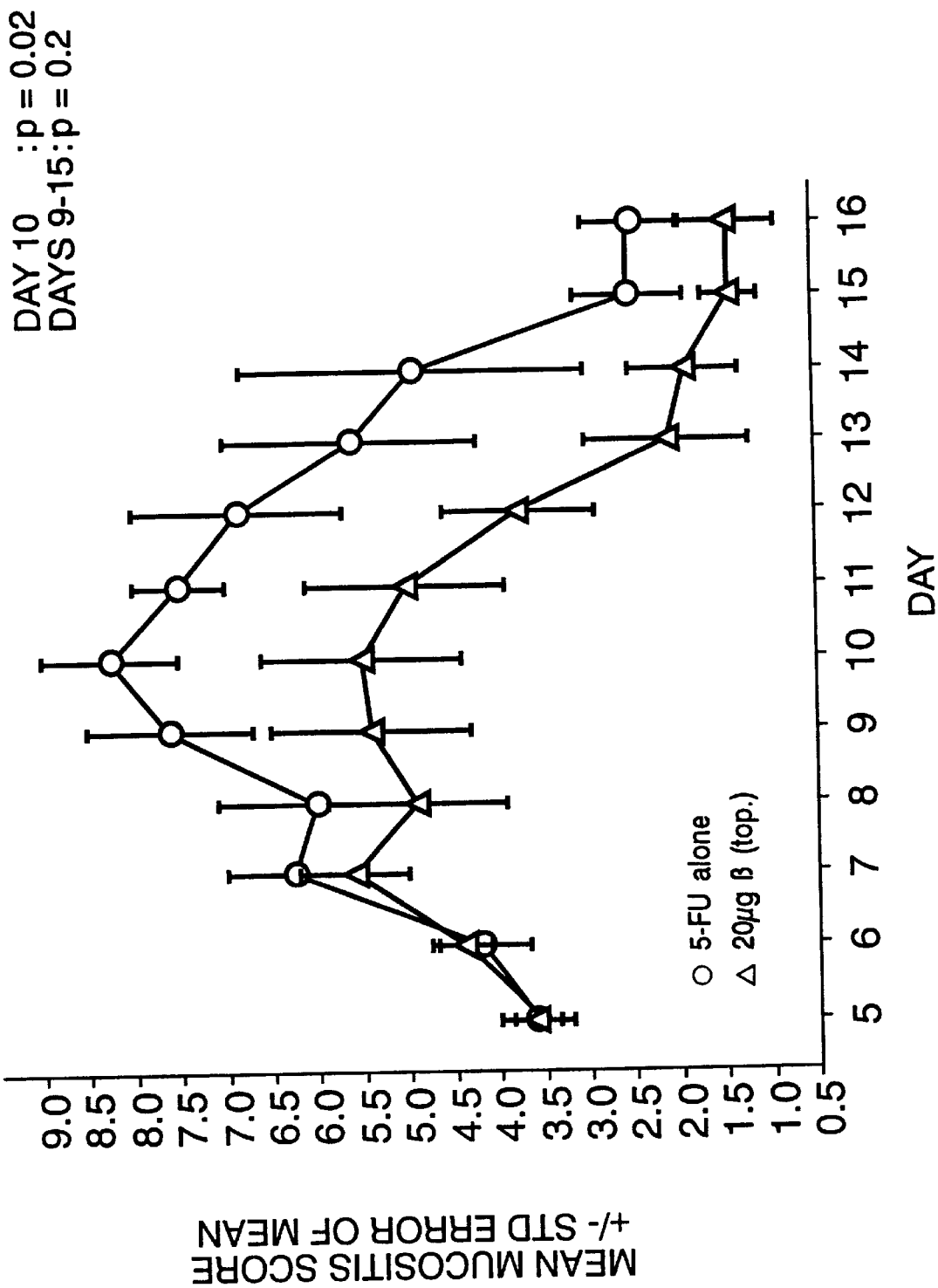
FIG. 5: Statistical significance data for Group 3: (open circles) treated with 5-FU alone. Group 3: (open triangles) 5-FU with 20 µg TGF-β3 topically. Error bars represent the standard error about the mean mucositis score.

As used herein, TGF-$\beta$ means a protein which exists in vivo as a covalently linked dimer having a molecular weight of approximately 25,000. The term TGF-$\beta$ means and includes natural and recombinant TGF-$\beta$1 (TIF, TIF-1), TGF-$\beta$2, TGF-$\beta$3 (TGI, TGI-1, TGI-2), TGF-$\beta$4, TGF-$\beta$5, or TGF-$\beta$ heterodimers including TGF-$\beta$1.2 and TGF-$\beta$2.3. The natural TGF-$\beta$ may be purified from tissue such as bone, platelets, or placenta or, more preferably prepared using recombinant technology (Iwata et al. 1992 A; ten Dijke et al. 1990 A; ten Dijke et al. 1990 B; Purchio et al., UK Patent Publication No. GB-2210620A; Derynck et al., U.S. Pat. No. 4,886,747; Jakolaw et al., 1988; Cerletti, N., 1991; Ogawa et al., 1992, McMaster et al. EP 542 679).

As used herein, Transforming Growth Factor Beta means and includes 1) TGF-$\beta$; 2) a biologically active homolog of TGF-$\beta$; 3) biologically active mutants of TGF-$\beta$; and 4) biologically active variants of TGF-$\beta$; and 5) biologically active fragments of any of 1) to 4). In this respect biologically active means having substantially the same biological activity as native TGF-$\beta$, e.g. binding to Type I or Type II TGF-$\beta$ receptors and inhibiting Mink Lung cell line CCL64. Mutants and variants may be polypeptides in which the amino acid sequence has been changed but are still biologically active including deletion mutants, substitution mutants, variants with amino acid substitutions. In addition, Transforming Growth Factor Beta means and includes variants capable of binding to the Type I or Type II receptors in which the biological activity has been mediated. Also, conjugates of Transforming Growth Factor which have altered biological properties such as increased half-life in vivo, increased activity, or both.

As used herein, stem cells include epithelial stem cells and hematopoietic stem cells. Hematopoietic progenitor cells are pluripotent cells capable of self renewal or differentiation into multiple hematopoietic cell lineages (e.g. erythroid cells, myeloid cells, etc.).

The present invention provides a method for inhibiting cytotoxic poisoning of normal cells in a subject which comprises administering to the subject an amount of a Transforming Growth Factor Beta effective to slow the growth of normal cells and thereby inhibit the cytotoxic poisoning of the normal cells in the subject. The normal cells may be epithelial cells, oral epithelial cells, epithelial cells lining the esophageal tract, lung epithelial cells, capillary endothelial cells, type I lung epithelial cells, gastrointestinal epithelial cells, colon crypt stem cells, stem cells, hematopoietic progenitor cells, or enterocytic cells (see Sonis, 1990, Stover, 1990).

Cytotoxic poisoning may be associated with antineoplastic therapy such as chemotherapy, or radiation therapy. Alternatively, cytotoxic poisoning may be a result of antiviral, anti-bacterial, anti-fungal, anti-microbial, anti-parasitic, or other therapeutics. The cytotoxic poisoning may be due to antiviral agents such as AZT, which causes mucositis (Posner, 1990).

In the present invention, the administration is initiated preferably prior to anti-neoplastic therapy for the subject. The anti-neoplastic therapy may be either chemotherapy or radiation therapy. Alternatively, the therapy may be any cytotoxic therapy. The invention is particularly suited to pediatric subjects. The administration may continue through a cycle of chemotherapy, for up to five days in order to retain its protective effect.

Radiation therapy is widely used in the treatment of various tumors but has many side effects including loss of rapidly proliferating epithelial cells e.g. of the oral cavity, GI tract, and the scalp. This leads to severe mucositis and alopecia in many cases.

Transforming Growth Factor Beta is useful in preventing epithelial cell damage during chemotherapy. Transforming Growth Factor Beta inhibits the proliferation of a variety of normal epithelial cell types and hematopoietic stem cells, in contrast to tumor cells which are often impaired in their ability to transduce signals mediated by TGF-$\beta$ binding to type I or type II TGF-$\beta$ receptors. Thus, tumor cells are generally less responsive to the growth inhibiting effects of TGF-$\beta$3. The ability of TGF-$\beta$3 to reversibly inhibit cycling of normal hematopoietic stem cell or epithelial cell types, but not many tumor cell types, allow TGF-$\beta$ to be used to as a chemoprotectant of normal tissue during cytotoxic chemotherapy. TGF-$\beta$3 mediated protection of the mucosa is valuable in reducing severe and painful mucositis. Implementation of this therapeutic approach represent a major advance in cancer management.

Growth modulation of hematopoietic cells by Transforming Growth Factor Beta is highly specific. Early hematopoietic stem cells stimulated by IL-1 and kit ligand (stem cell factor SCF, mast cell growth factor, MGF) are inhibited by Transforming Growth Factor Beta, whereas the proliferation of later cell lineages stimulated by GM-CSF are potentiated by Transforming Growth Factor Beta. Based on in vitro and in vivo experiments, Transforming Growth Factor Beta plays a pivotal role in the ultimate goal of coupling stem cell expansion and protection strategies with accelerated effector cell regeneration.

Transforming Growth Factor Beta may be administered in several ways to effect hematopoietic chemoprotection. Transforming Growth Factor Beta is administered during or immediately prior to chemotherapy to protect the early hematopoietic stem cell population in multicycle or accelerated cycle chemotherapy. Hematopoietic growth factors may be used in the recovery phase to accelerate repopulation of the macrophage/granulocyte lineages. Transforming Growth Factor Beta treatment prevents long term stem cell depletion, neutropenia and produces a continued patient tolerance to further cycles of chemotherapy.

In addition, hematopoietic growth factors can be administered prior to chemotherapy to effect an increase in total bone marrow cellularity and effect an increase the number of hematopoietic cells surviving cytotoxic chemotherapy. However, expanding the hematopoietic stem cell population using positive growth factors (for example kit ligand or stem cell factor) requires a mechanism to restore these cycling cells back to a non-dividing state prior to chemotherapy. Transforming Growth Factor Beta administered to this expanded population of hematopoietic stem cells prior to chemotherapy acts to protect and increase the reserve of the more mature hematopoietic cells. Thus, Transforming Growth Factor Beta may reduce the fall in white blood cell count associated with chemotherapy.

For oral mucositis, the preferable administration is topical. Dose ranges for topical use include 1 ng to 10 mg per dose, preferably, 100 ng to 2 mg per dose or more preferably 10 μg to 500 μg per dose. However, the administration may also be systemic. Dose ranges for systemic application include 1 g to 500 μg/kg subject weight/day, preferably 80 g to 100 μg/kg subject weight/day, or more preferably 1 μg to 20 μg/kg subject weight/day.

Chemotherapy agents which cause mucositis include, but are not limited to 5-FU, Ara-C, doxorubicin (Adriamycin) daunorubicin, methotrexate, vincristine, vinblastine, Melphalan, cytosine arabinoside, thioguanine, bleomycin, dactinomycin, cisplatin, mithramycin, mitomycin, hydroxyurea and procarbazine hydrochloride (See also Table A). Patients receiving either high dose or accelerated cycle chemotherapy are at risk of developing mucositis, as are pediatric patients, patients undergoing bone marrow transplantation and patients receiving radiation therapy, especially those receiving therapy for squamous carcinoma of the head and neck.

Alternatively, administration may be by tissue-specific, locally activated mutant proTGF-βs. For example, the mutant TGF-β3 precursor is expressed as a single homodimeric polypeptide in a host cell by mutation of the R-K-K-R (SEQ I.D. NO.:1) cleavage site between the TGF-β3 pro region and mature TGF-β3 to a protease cleavage site, e.g. factor Xa cleavage sequence (Ile-Glu-Gly-Arg) (SEQ I.D. NO.:2) or a collagenase cleavage sequence (Pro-X-Gly-Pro) (SEQ I.D. NO.:3) using standard site directed mutagenesis procedures, followed by insertion of the mutant TGF-β3 nucleic acid into a expression vector and transfection of the mutant TGF-β3/vector DNA into a host cell (e.g. E. coli, CHO, or HeLa) together with DNA encoding a selectible marker (e.g. neo, dhfr). Alternatively, the cleavage site may be any specifically cleaved sequence as exemplified but not limited to the following examples: Ala64-Subtilisin (His-X-X-X-Trp) (SEQ I.D. NO.:4), a chymotrypsin (Tyr-Phe), a enteropeptidase (Gly[Asp]$_{3-5}$ Lys) (SEQ I.D. NO.:5), a Factor XIIa (Ile-Val-Gly-Gly-Thr-Val) (SEQ I.D. NO.:6), a plasma kallikrein (Pro-Phe-Arg), or a thrombin (Gly-Pro-Arg) (SEQ I.D. NO.:8) (Nilsson et al., 1988). These locally activated Mutant proTGF-βs may be used to deliver TGF-β to a precise organ target. The mutant proTGF-βs may reduce toxicity associated with non-specific TGF-β dose regimens. Similar mutants may be made for TGF-β1, TGF-β2, TGF-β4, or TGF-β5.

An "effective amount" as used herein refers to that amount which provides a prophylactic effect by preventing cytotoxic poisoning of normal cells or mucositis in a subject receiving a given condition and administration regimen. Pharmaceutically-acceptable acid addition salts of the compounds of this invention include, but are limited to, those formed with HCl, HBr, HNO$_3$, H$_2$SO$_4$, H$_3$PO$_4$, CH$_3$SO$_3$H, p-CH$_3$C$_6$H$_4$SO$_3$H, CH$_3$CO$_2$H, gluconic acid, tartaric acid, maleic acid and succinic acid. Pharmaceutically-acceptable cationic salts of the compounds of this invention include, but are not limited to, those of sodium, potassium, calcium, magnesium, ammonium, N,N'-dibenzylethylenediamine, N-methylglucamine (meglumine), ethanolamine and diethanolamine.

For administration to humans in either a curative or prophylactic treatment of mucositis or other conditions, oral dosages of the compounds are generally in the range of from 0.1–100 mg daily for an average adult patient (70 kg). Thus, for a typical adult patient, individual tablets or capsules contain from 0.1 to 50 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice, the physician will determine the actual dosage which will be most suitable for an individual patient and it will vary with the age, weight, and response of the particular patient. The above dosages are exemplary of the average case but there can, of course, be individual instances where higher or lower dosage ranges are merited, and all such dosages are within the scope of this invention.

For human use, the compounds of this invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in an admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

In addition, compositions comprising prophylactically effective amounts together with suitable diluents, preservatives, solubilizers, emulsifiers, adjuvants and/or carriers useful for Transforming Growth Factor Beta therapy. Such compositions are liquids or lyophilized or otherwise dried formulations and include diluents of various buffer content (e.g., Tris-HCl, acetate phosphate), pH and ionic strength, additives such as albumin or gelatin to prevent absorption to surfaces, detergents (e.g., Tween 20, Tween 80, Pluronic F68, Pluronic F127, bile acid salts), solubilizing agents (e.g., Thimerosal, benzyl alcohol), bulking substances or tonicity modifiers (e.g., lactose, mannitol), covalent attachment of polymers such as polyethylene glycol to the Transforming Growth Factor Beta, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of Transforming Growth Factor Beta. Other ingredients optionally may be added such as antioxidants, e.g., ascorbic acid, L-cysteine, sodium sulfite; low molecular weight (less than about ten residues) polypeptides, e.g., polyarginine or tripeptides; proteins, such as serum albumin, gelatin, or immunoglobulins; amino acids; such as glycine, glutamic acid, aspartic acid, or arginine; chelating agents such as EDTA; and sugar alcohols such as mannitol or sorbitol. The choice of composition will depend on the physical and chemical properties of the Transforming Growth Factor Beta. Controlled or sustained release compositions include formulation of lipophilic depots (e.g., fatty acids, waxes, oils). See also U.S. Pat. No. 5,213,811 for sustained release formulations. The invention also includes particulate compositions coated with polymers (e.g., poloxamers or poloxamines). The Transforming Growth Factor Beta may be coupled to antibodies, ligands, antigens, or targeted against tissue-specific receptors. Other embodiments of the compositions of the invention incorporate particulate forms protective coatings, protease inhibitors, or permeation enhancers for various routes of administration, including parenteral, pulmonary, nasal, buccal and oral.

Transforming Growth Factor Beta may be administered by pulmonary absorption using commercially available nebulizers for liquid formulations. The nebulizers may be jet nebulizers or ultrasonic nebulizers. Liquid formulations may be directly nebulized or lyophilized powder nebulized after reconstitution. A liquid formulation may be directly instilled into the nasotracheal or endotracheal tubes in intubated patients. Alternatively, Transforming Growth Factor Beta may be aerosolized using a fluorocarbon formulation and a metered dose inhaler. It may also be inhaled as a lyophilized and milled powder.

As described above, the Transforming Growth Factor Beta may be modified by conjugation with polyethylene glycol. In a typical preparation methoxypolyethylene glycol-succinimydyl succinate (18.1 mg- 3.63 $\mu$mol; SS-MPEG= Sigma Chemical Co. No. M3152), molecular weight approximately 5,000) is dissolved in 0.32 mL deionized water is added to 13.0 mg (1.16 $\mu$mol) TGF-β in 1.0 mL 138 $\mu$M sodium phosphate, 62 mM NaCl, 0.62 mM sodium acetate, pH 8.0. The resulting solution is shaken gently (100 rpm) at room temperature for 30 minutes. A 1.0 mL aliquot of the reaction mixture (10 mg protein) is applied to Pharmacia Superdex 75 gel filtration column (1.6 ×50 cm) and eluted with 100 mM sodium phosphate, pH 6.9 at a rate of 0.25 mL/min. Fractions are collected and monitored by UV. See also U.S. Pat. Nos. 5,206,344, 4,261,973, 4,609,546, and 4,179,337.

Suitable topical formulations include gels, creams, solutions, emulsions, carbohydrate polymers, biodegradable matrices thereof; vapors, mists, aerosols, or other inhalants. Vapors, mists, aerosols, or other inhalants are particularly suited for inhibiting pulmonary toxicity. Transforming Growth Factor Beta may be encapsulated in a wafer, wax, film or solid carrier, including chewing gums. Permeation enhancers to aid in transport to movement across the epithelial layer are also known in the art and include, but are not limited to, dimethyl sulfoxide, sodium dimethyl glycolate, glycols, and sodium glycolate. Suitable vehicles are described above. The Transforming Growth Factor Beta so administered may be immobilized so as to prevent dilution and washing by saliva. Such agents are also known in the art and include but are not limited to methyl-dimethyl sulfoxide, glycols and propylcellulose and the like. The Transforming Growth Factor Beta may also be administered in the form of an oral wash (see Eisen, D. et al., 1990). Alternatively, the Transforming Growth Factor Beta may be administered in a pectin-based gel such as Orabase™.

Rectal preparations for GI protection are also prepared by conventional techniques, for example by employing an oleaginous base such as a higher fatty acid glyceride e.g., cocoa butter, Witepsols (a semisynthetic base, Dynamite Nobel, Federal Republic of Germany); a medium fatty acid glyceride e.g., Miglyols (Dynamite Nobel); or a vegetable oil e.g., sesame oil, soybean oil, corn oil, cottonseed oil, olive oil. Suitable enteric coating formulations are exemplified by U.S. Pat. Nos. 5,104,430 (Dupont-Merck), 5,096,717 (Ciba-Geigy), 4,713,248 (Benzon) and 5,178,866 (Alza).

The disclosures of these patent specifications are hereby incorporated in their entireties. Further examples of enteric coating formulations are found in European Patent applications EP 475536 (Takeda Chemical) and EP 244,380 (Haessle).

For the prevention of alopecia, Transforming Growth Factor Beta will be typically administered systemically, however, it may also be administered topically in a solution, cream, ointment, gel, lotion, shampoo or aerosol adapted for application to the skin. These pharmaceutical compositions will contain about 0.01 $\mu$g to about 100 $\mu$g /day/cm$^2$, preferably about 0.1 $\mu$g to about 10 $\mu$g/day/cm$^2$ of active compound in a pharmaceutical carrier.

For topical application various other pharmaceutical formulations or carriers are useful for the administration of the active compound of this invention. Such formulations include, but are not limited to the following: ointments such as hydrophilic petrolatum or polyethylene glycol ointment; pastes which may contain gums such as xanthan gum; solutions such as alcoholic, aqueous or buffered solutions; gels such as aluminum hydroxide or sodium alginate gels; albumins such as human or animal albumins; collagens such a human or animal collagens; celluloses such as alkyl celluloses, hydroxyalkyl celluloses and alkylhydroxyalkyl celluloses, for example methylcellulose, hydroxyethyl cellulose, carboxymethyl cellulose, hydroxypropyl methylcellulose, and hydroxypropyl cellulose; polymers such as Pluronic R Polyols exemplified by Pluronic F-127; tetronics such as tetronic 1508; and alginates such as sodium alginate.

The present invention also provides a method of obtaining bone marrow substantially free of actively dividing tumor cells which comprises: (a) contacting bone marrow containing normal hematopoietic cells and actively growing tumor cells with an effective amount of a Transforming Growth Factor Beta such that the growth of the normal hematopoietic cells is temporarily inhibited; (b) subsequently contacting bone marrow with a tumor inhibiting drug under such conditions to permanently prevent growth of tumors cells; and (d) culturing bone marrow so as to permit growth of normal hematopoietic cells thereby obtaining bone marrow substantially free of actively dividing tumor cells.

Additionally, the present invention provides a method of obtaining bone marrow substantially free of actively dividing tumor cells. The method comprises (a) contacting bone marrow containing normal hematopoietic cells and actively growing tumor cells with an effective amount of a Transforming Growth Factor Beta; (b) culturing bone marrow of step (a) in the presence of Transforming Growth Factor Beta for a suitable period, under conditions such that terminal cell differentiation and clearance of tumor cells is permitted; and (e) obtaining bone marrow substantially free of actively growing tumor cells.

This invention is illustrated in the Experimental Detail sections which follow which show that Transforming Growth Factor Beta inhibits cytotoxic poisoning of normal cells in a subject. These sections are set forth to aid in an understanding of the invention but are not intended to, and should not be construed to limit in any way the invention as set forth in the claims which follow.

EXPERIMENTAL DETAILS

EXAMPLE 1

Assays of Transforming Growth Factor Beta Activity In Vitro on Several Human Epithelial Tumor Cell Lines and Human Fibroblasts Cell growth was determined using the monolayer assay for Transforming Growth Factor Beta described by Iwata (Iwata et al. 1992 B). Non-leukemic cells were subcultured on 96-well tissue culture plates in 100 µl of media at a seeding density of 2×10³ cells per well. Cells were maintained and assayed in Dulbecco's modified Eagle's medium containing 10% fetal bovine and 2% L-glutamine. These cells were treated with 25 ng/ml (~1 nM) of TGF-β3, pulsed 24 hours with 1 µCi/ml 5-[¹²⁵I]-iodo-2' deoxyuridine when cells in the untreated control wells were 90% confluent and harvested. Table 2 shows inhibition of some human epithelial tumor lines by Transforming Growth Factor Beta. In contrast, normal epithelial cells are strongly inhibited at picomolar concentrations of TGF-β3.

TABLE 2

Effects of TGF-β3 (1 nM) on the Growth of Human Epithelial Derived Cancer Cell Lines in Culture

| CELL LINE | % INHIBITION |
|---|---|
| Human Epithelial Derived Cancer Lines | |
| A549 (lung adenocarcinoma) | 46 |
| A375 (melanoma) | 47 |
| A2058 (melanoma) | 88 |
| WiDR (colon adenocarcinoma) | 24 |
| MCF 7 (breast carcinoma) | 57 |
| Normal Human | |
| Huf (foreskin fibroblasts) | 6 |

Fibroblasts behave in a manner opposite normal epithelial cells in this assay.

In a similar manner, the effect of TGF-β1, TGF-β2, TGF-β4, and TGF-β5 on human tumor lines is also assayed.

EXAMPLE 2

In Vitro Protection of Epithelial Cells Against Chemotherapeutic Drugs (FIGS. 1A and 1B)

In order to evaluate Transforming Growth Factor Beta as a protective agent in vitro the following experiments were performed.

Mink cells were seeded in 96-well plates at 10³ cells/well in 100 µl of DMEM supplemented with 10% fetal bovine serum. Wells containing treated cells received 25 µl of TGF-β3 (50 ng/ml). After 24 hours incubation with TGF-β3, 25 µl of either colchicine or vinblastine were added. After another 24 hours, the media was removed and the cells washed once with Dulbecco's PBS and fresh complete media added. The cells were incubated for another 7 days.

Cell growth was quantitated by uptake of 5-[¹²⁵I]iodo-2' deoxyuridine (¹²⁵IUdR) indicating the amount of cell growth as described (Iwata et al., 1992 B). As seen in FIG. 1, cells preincubated with TGF-β3 prior to incubation with various doses of chemotherapeutic drugs (e.g. vinblastine and colchicine) showed significantly more uptake of ¹²⁵IUdR relative to cells which were incubated with the chemotherapeutic drugs without TGF-β3. Therefore, cells preincubated with TGF-β3 were protected from the toxic effects of the chemotherapeutic drugs. Similar results were observed when adriamycin was used as the chemotherapeutic drug. This protective effect would also be expected with any other chemotherapeutic drugs (which preferentially kill actively dividing cells).

For Transforming Growth Factor Beta to be effective in protecting normal epithelial cells from chemotherapy it is apparent that the growth of the tumor is preferably less inhibited than that of normal tissues. This is achieved either because tumors are either innately resistant or less sensitive to the growth inhibitory effects of Transforming Growth Factor Beta. Alternatively, the pharmacokinetics of Transforming Growth Factor Beta administration allow a differential effect between normal and tumor cells in vivo.

In a similar manner, TGF-β1, TGF-β2, TGF-β4, and TGF-β5 is assayed for protective activity.

EXAMPLE 3

In Vivo Inhibition of Oral Epithelial Proliferation by Topical Application of Transforming Growth Factor Beta We show topical administration of Transforming Growth Factor Beta to the buccal cavity of hamsters acts to decrease the fraction of oral epithelial cells in S-phase, and thereby inhibit cell proliferation. In this example the buccal pouch of Golden Syrian hamsters were treated with 0 µg, 2 µg, 20 µg or 200 µg of TGF-β3 in a saline diluent and subsequently covered with methyl-propylcellulose.

Three topical TGF-β3 applications were made over an eight hour time period. Only the left cheek was treated with TGF-β3; the right cheek served as a control. Biopsies of the cheek pouch were obtained approximately 16 hours after the final TGF-β3 treatment. The biopsied oral tissue was formalin fixed, embedded in paraffin, sectioned and immunohistologically stained with a monoclonal antibody to PCNA (a marker of S-phase cells). Alternatively, Ki67 antibody staining of sectioned tissue or ³H-thymidine labelling of the oral epithelium in vivo may be used to measure cell division in vivo. Sixteen hours post TGF-β3 treatment the following data was obtained (Table 3):

TABLE 3

In vivo Inhibition of Oral Epithelial Proliferation shown by PCNA Staining of Hamster Oral Mucosa after Topical Administration of TGF-β3.

| Topical Treatment | Mean Inhibition vs. Control |
|---|---|
| 2 µg TGF-β3 | 22% |
| 20 µg TGF-β3 | 42% |
| 200 µg TGF-β3 | 46% |

These data show Transforming Growth Factor Beta to be a potent inhibitor of the cell cycling of oral epithelium in vivo.

The in vivo activity of TGF-β1, TGF-β2, TGF-β4, and TGF-β5 is evaluated in a similar manner.

EXAMPLE 4

Transforming Growth Factor Beta as an Agent Useful for the Prevention of Epithelial Cell Damage Caused by Chemotherapy or Radiotherapy An animal model is used to evaluate in vivo efficacy of Transforming Growth Factor Beta as an agent useful for prevention of oral mucositis in hamsters induced by the chemotherapeutic agent 5-FU (Sonis et al., 1990). A number of 5-FU schedules may be useful to produce mucositis and assess therapeutic standards. In one protocol, groups of 12, eight week old Golden Syrian hamsters are given 5-FU (60 mg/kg) on days 0, 5 and 10. Alternatively, 5-FU may to administered on days 0 and on day 2 by the intraperitoneal (i.p.) route in doses of 60 mg/kg and 40 mg/kg, respectively. Animals are observed and weighed daily. The animals are anesthetized with ether and the buccal cavity everted and photographed. Photographs of the cheek pouch are numbered, randomized, independently scored blind using a common set of grading photographs. This approach, grading oral mucositis on scale from 1 to 10, allows statistically significant data. In hamsters as in man, oral mucositis peaks around 7 days from initial exposure to 5-FU. Importantly, oral mucositis is worse when the epithelium is actively dividing (e.g. when TGF-α pretreated), mimicking the situation with pediatric patients undergoing chemotherapy.

Prevention of oral mucositis is shown by pretreatment of hamsters with Transforming Growth Factor Beta prior to 5-FU treatment. Mucositis is graded on a scale of 1 to 10 as described above. Schedule and dose relationship to efficacy is demonstrated using the same animal protocol.

In this example TGF-β3 was administered to the hamster oral cavity to prevent mucositis. Transforming Growth Factor-beta was applied either in solution or as a suspended precipitate. For example, a precipitate in a suspension was prepared by addition of 20 μg of TGF-β3 in 2 mM HCl, 0.1% Tween 80 in a volume of 100 μl to 1 ml of phosphate buffered saline (PBS) pH 7.4. The following groups of 10 Golden Syrian hamsters (age approximately 6 week) were evaluated for the severity and duration of mucositis following 5-FU treatment using the days 0 and 2 schedule described above. The following groups were evaluated:

TABLE 4A

| Group (N = 10) | TGF-β3 | Dose Schedule | Route |
|---|---|---|---|
| 1 | 4 × vehicle alone | over 24 hrs. day −1 to day 0 | topical |
| 2 | 4 × 2 μg | over 24 hrs. day −1 to day 0 | topical |
| 3 | 4 × 20 μg | over 24 hrs. day −1 to day 0 | topical |
| 6 | 3 ' 4 μg | over 8 hrs. day 2 | intra-peritoneal |

Figure 6:
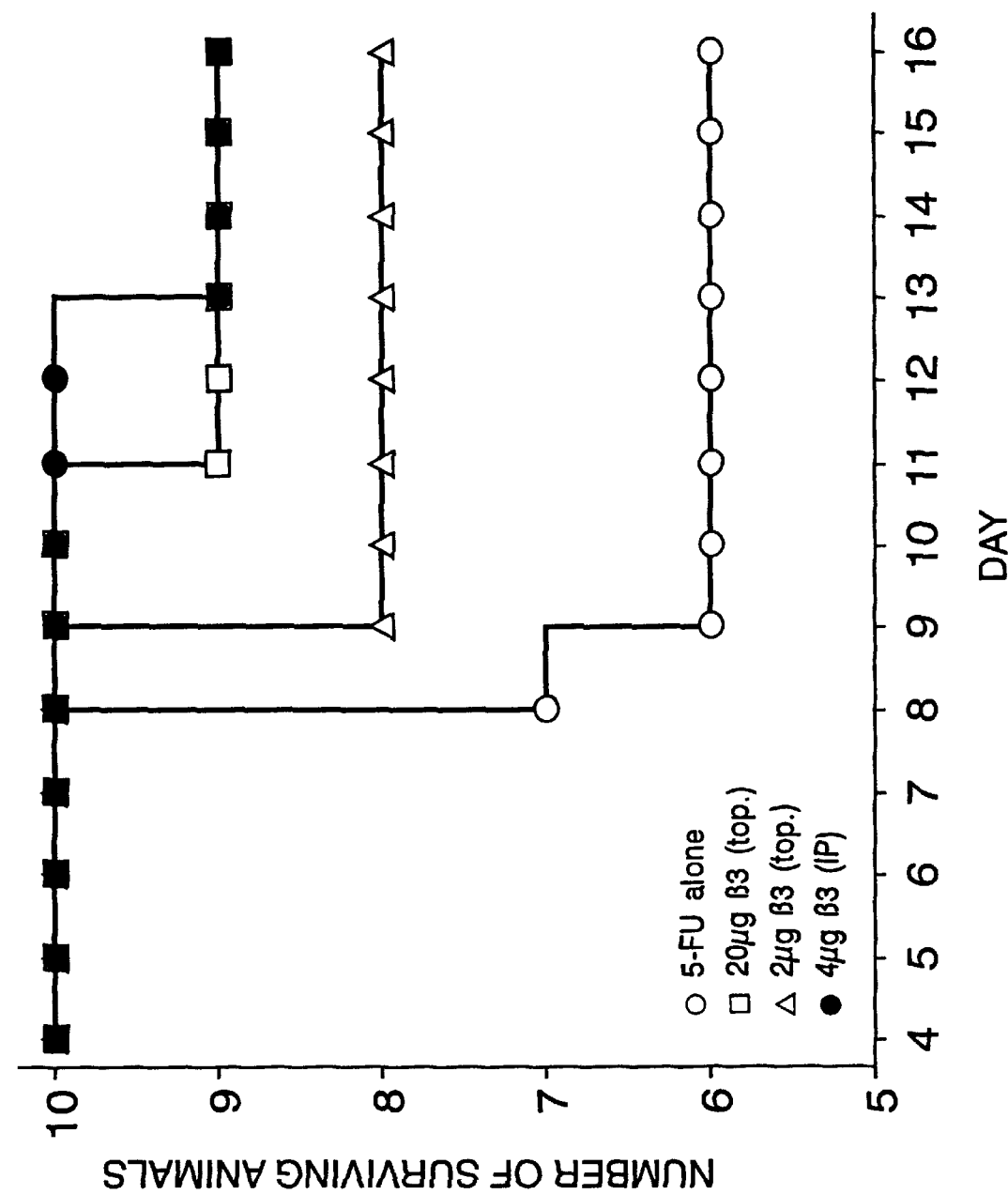
FIG. 6: Survival data days 4–16 for Group 1: (open circles) treated with 5-FU alone. Group 2: (open triangles) 5-FU+2 µg TGF-β3 topically. Group 3: (open squares) 5-FU and 20 µg TGF-β3 topically. Group 6: (solid circles) 5-FU and 4 µg TGF-β3 intraperitoneally.
Figure 7:
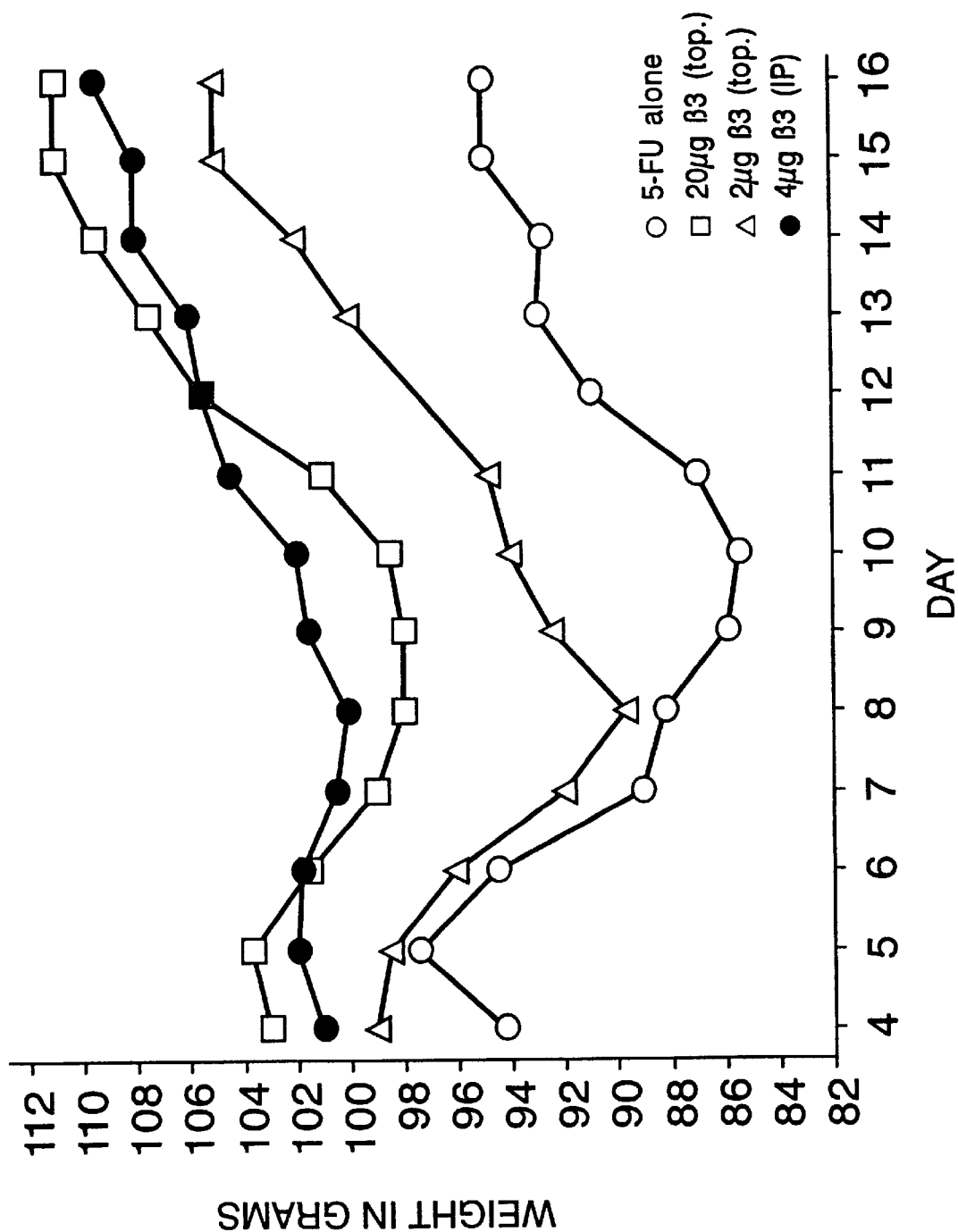
FIG. 7: Average weight curves for days 4–16. Group 1: (open circles) treated with 5-FU alone. Group 2: (open triangles) 5-FU and 2 µg TGF-β3 topically. Group 3: (open squares) 5-FU and 20 µg TGF-β3 topically. Group 6: (filled circles) 5-FU and 4 µg TGF-β3 intraperitoneally.

These data were statistically significant and conclusively show TGF-β reduces the severity and duration of mucositis in vivo (FIGS. 2A–5). Increased survival (FIG. 6) and weight retention (FIG. 7) were also observed. This effect was achieved through cell cycle inhibition of the oral epithelium prior to chemotherapy, and not apparently by accelerated wound healing, as shown by Example 5 below.

Groups of ten three to four week old Golden Syrian hamsters were injected i.p. with 80 mg/kg 5-FU on day zero and 60 mg/kg 5-FU on day 2. TGF-β1, TGFβ2 or TGFβ3 was administered to the hamster oral cavity to prevent mucositis. The following groups were evaluated for the severity and duration of mucositis following 5-FU treatment:

TABLE 4B

| Group | TGF-β1,2 or 3 | Dose Schedule | Route |
|---|---|---|---|
| 1 | 4 × vehicle alone | over 24 hrs. day −1 to day 0 | topical |
| 2 | 4 × 20 μg TGFβ1 | over 24 hrs. day −1 to day 0 | topical |
| 3 | 4 × 20 μg TGFβ2 | over 24 hrs. day −1 to day 0 | topical |
| 4 | 4 × 20 μg TGFβ3 | over 24 hrs. day −1 to day 0 | topical |

These initial data show that Transforming Growth Factor Beta increased survival by day 8. Mucostis score was also decreased.

TABLE 4C

| Group | Mean Survival |
|---|---|
| 1 | 42% |
| 2 | 70% |
| 3 | 70% |
| 4 | 60% |

The effective amount of Transforming Growth Factor Beta in the carrier vehicle ranges from 0.01 μg to 10 mg depending on the extent or severity of the oral mucositis. Transforming Growth Factor Beta is applied to the buccal cavity in a suitable physiological carrier up to 5 days prior to treatment with one or more cytotoxic chemotherapy agents.

EXAMPLE 5

Effect of Additional Transforming Growth Factor Beta Administration After 5-FU Treatment To evaluate the effects of Transforming Growth Factor Beta post second 5-FU treatment as used for normal wound healing agents, two additional groups were treated in the same way as Groups 2 and 3, but also receiving topical, oral Transforming Growth Factor Beta following the second dose of 5-FU as shown in Table 5.

TABLE 5

| Group | TGF-β3 post 5-FU | Time of TGF-β3 | Route |
|---|---|---|---|
| 4 | 6 × 2 μg | twice daily days 5, 6 and 7 | topical |
| 5 | 6 × 20 μg | days 5, 6 and 7 | topical |

Similar experiments are performed with TGF-β1, TGF-β2, TGF-β4, and TGF-β5.

Figure 8:
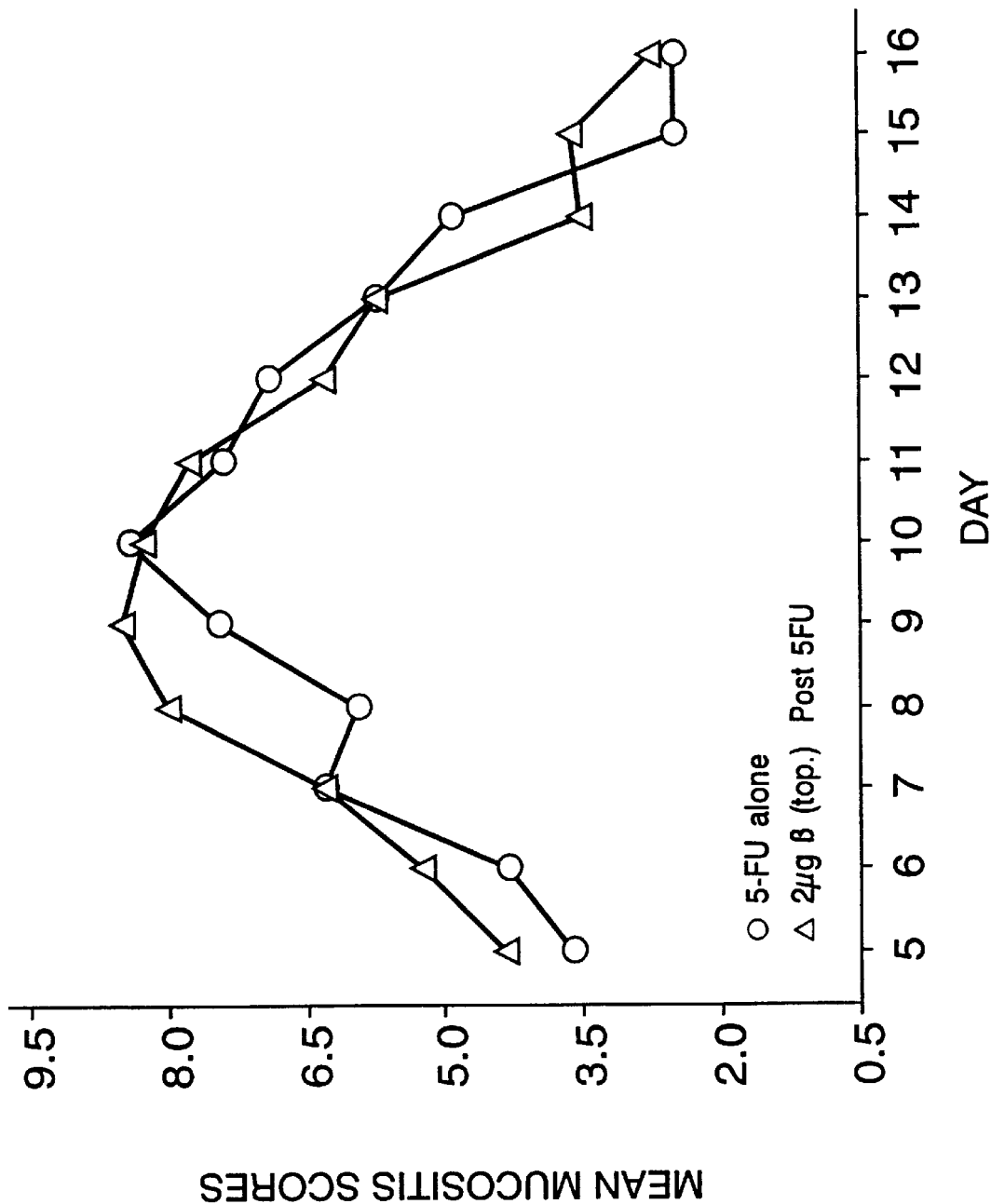
FIG. 8: Mean mucositis scores for Group 1: (open circles) 5-FU alone. Group 4: (open triangles) 5-FU and additional 2 µg TGF-β3 topically administered post-5-FU, twice daily on days 5, 6 and 7.
Figure 9:
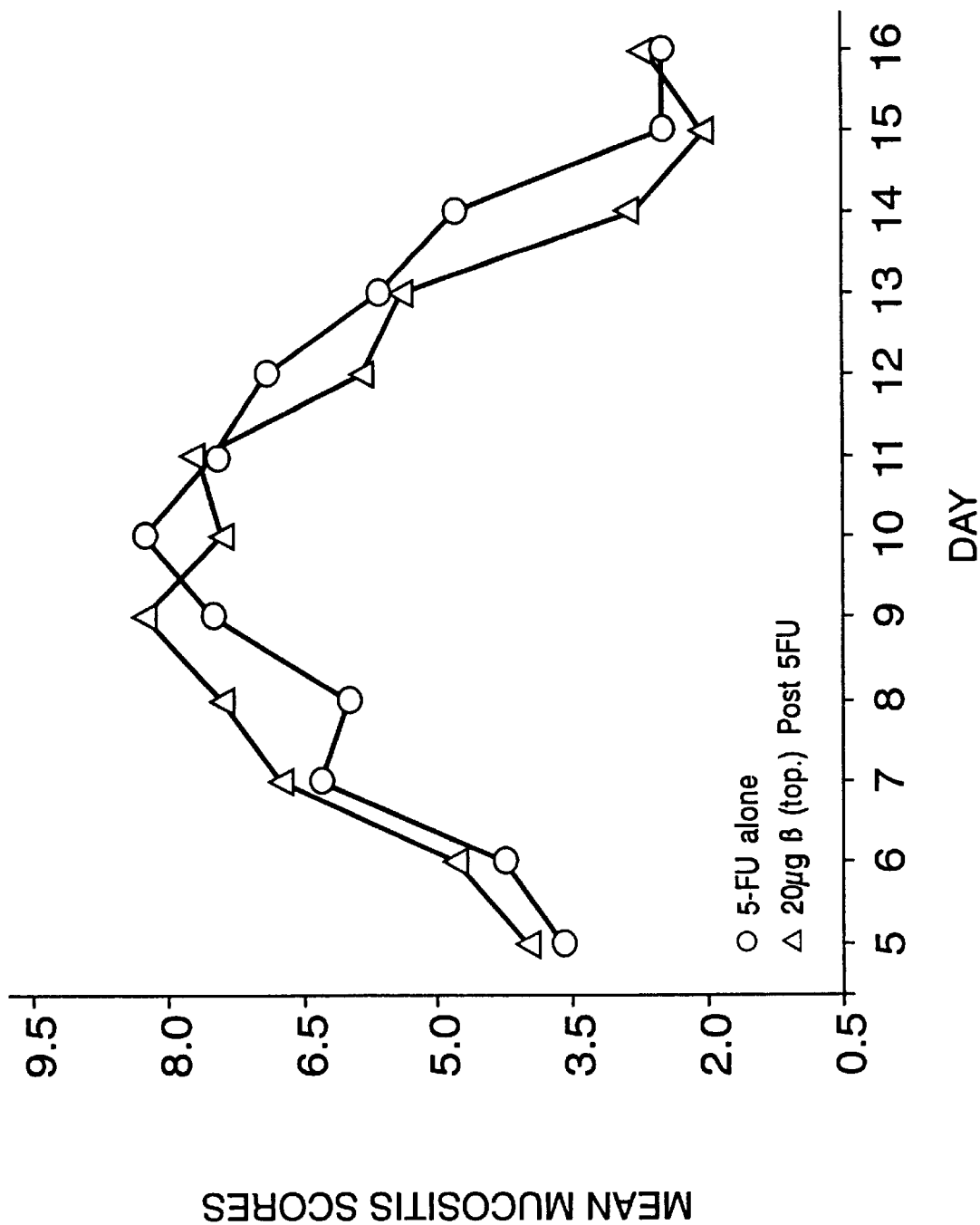
FIG. 9: Mean mucositis scores for Group 1 (open circles): 5-FU alone. Group 5: (open triangles) 5-FU and additional 20 µg TGF-β3 topically administered post 5-FU, twice daily on days 5, 6 and 7
Figure 10A:
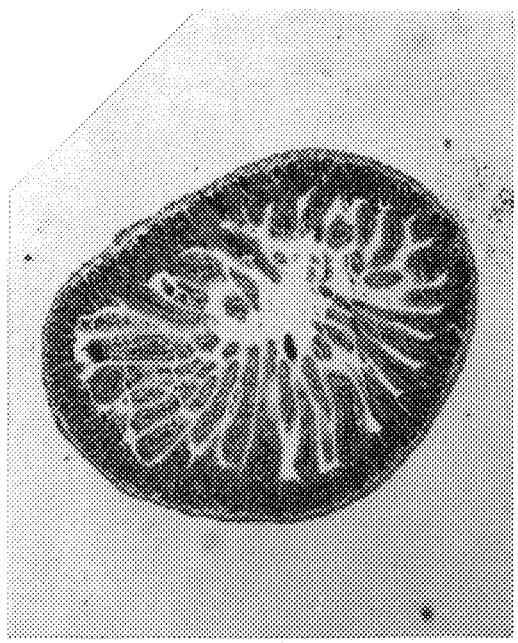
Figure 10B:
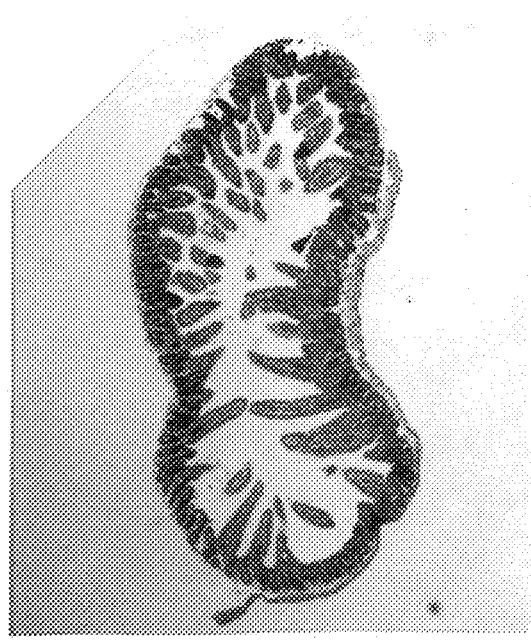
Figure 10C:
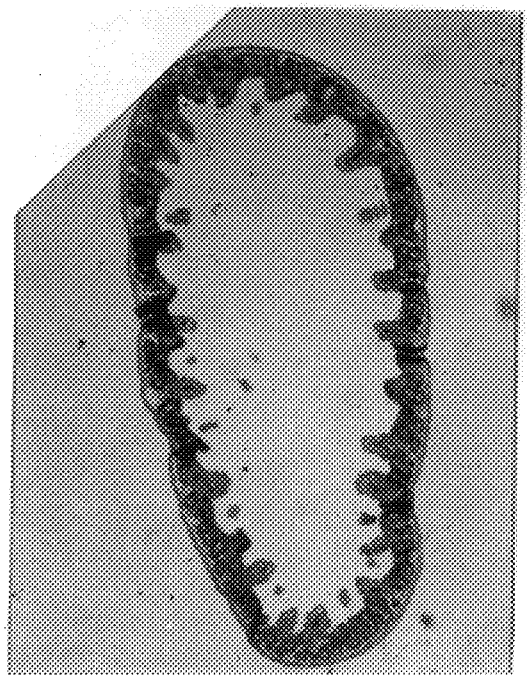
Figure 10D:
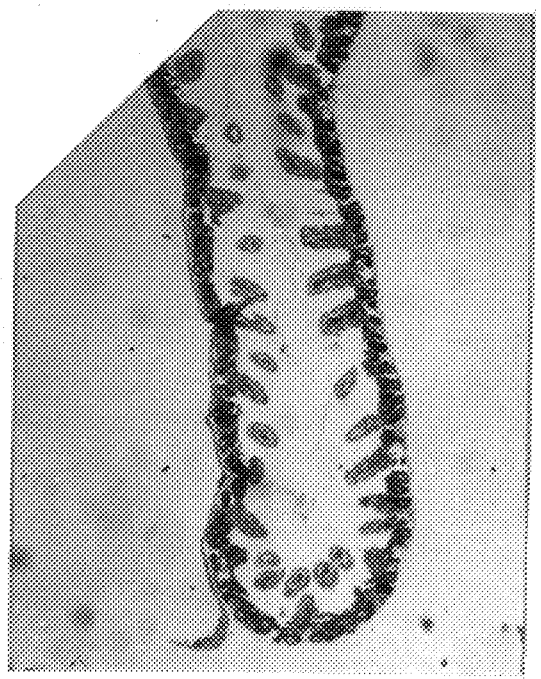
FIGS. 10D and 11A–11F: Effects of TGF-β3 on mouse gastrointestinal epithelium in vivo.
Figure 11A:
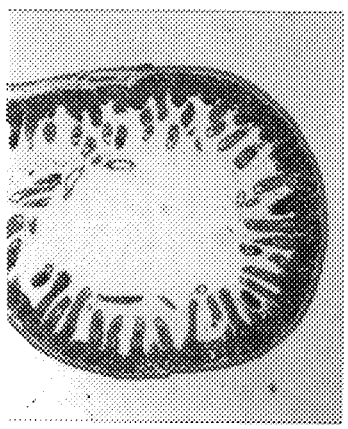
Figure 11B:
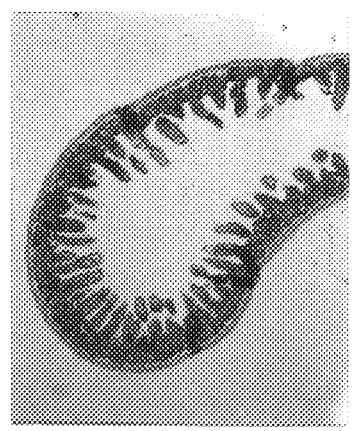
Figure 11C:
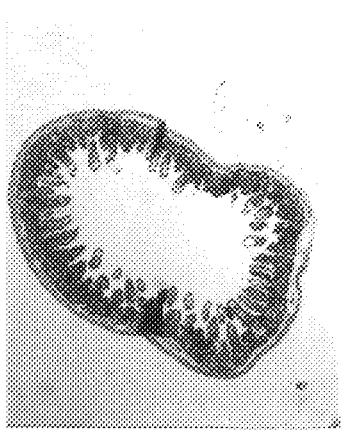
Figure 11D:
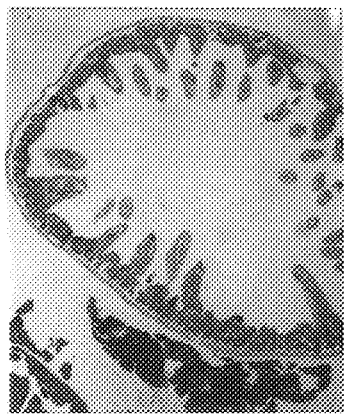
Figure 11E:
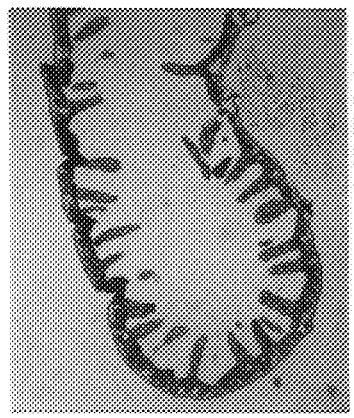
Figure 11F:
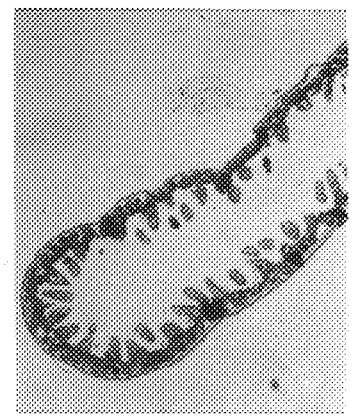

TGF-β post 5-FU administration was not effective in preventing mucositis as shown in FIGS. 8 and 9. No significant differences in mucositis scores were observed between groups 1, 4 and 5. Thus, unlike TGF-α, EGF, or PDGF, administration of topical Transforming Growth Factor Beta after chemotherapy has no beneficial therapeutic effect, unlike TGF-β pre-treatment, and therefore is contraindicated. In this setting and dose TGF-β is a negative regulator of epithelial cell growth, not a positive growth factor for oral tissue in contrast to TGF-α, EGF, and PDGF.

EXAMPLE 6

Topical Application of Transforming Growth Factor Beta and Cell Cycling of Hamster Oral Epithelia in vivo The effect of TGF-β3 on proliferation of oral epithelium was evaluated, both in vitro by measurement of DNA synthesis in cultured hamster oral epithelium and in vivo by measurement of bromodeoxyuridine incorporation and PCNA expression in the hamster cheek pouch. First, short term cultures of oral epithelium (>90%) were established in KBM media (Clonetics), 2.5% FCS and incubated with 0, 1, 100 or 1000 pM TGF-β3 for 48 hours. DNA synthesis was measured by addition of $^{125}$Iodo-deoxyuridine (1 μCi/ml) for an additional 48 hours as previously described (Iwata et al. 1985). Exposure to 100 pM or 1 nM TGF-β3 reduced label incorporation to 43% and 23% of the untreated control value respectively.

In vivo, the effect of Transforming Growth Factor Beta on cell cycling of oral epithelium was investigated by two methods. First, the fraction of oral epithelial cells undergoing DNA synthesis was measured after topical application of TGF-β3 (4 doses of 20 μg in saline over 24 hours) to the hamster cheek pouch (Table 5). Hamsters were injected with bromo-deoxyuridine (BrdU; 5 mg, ip) at 0, 16 and 54 hours post TGF-β3 treatment. Animals were sacrificed 2 hours post BrdU administration, and cheek pouch sections (4m) stained with anti-BrdU antibody (Amersham). The proliferative, self renewal component in oral epithelium has been shown to be clustered, separated by non-dividing regions (Gibbs and Casarett, 1972; Bickenbach and MacKenzie, 1984). BrdU labelled and unlabeled cells from random fields (n>25) containing >1 labelled cell were counted under the light microscope and an S-phase fraction or labelling index (LI) was calculated. Topical application of TGF-β3 reduced the LI to 44% and 51% of mock treated hamsters at 0 and 16 hours respectively. Second, the number of cheek pouch epithelial cells expressing proliferating cell nuclear antigen (PCNA) was determined. PCNA is apparently tethered to the nucleus during S-phase in a form resistant to acid extraction and has been used as a general marker of DNA synthesis in tissue sections. Tissue samples were collected 16 hours after topical application of 20 μg TGF-β3 to the left cheek pouch. The untreated right pouch served as control. Sections were prepared and developed with anti-PCNA monoclonal antibody, anti-mouse Ig and DAB (Oncogene Science). Cells in the epithelial layer staining either positive or negative for PCNA were counted under the light microscope from multiple fields (n=30). Results are shown in Table 6. Application of 20 μg of TGF-β3 resulted in a reduction in the PCNA positive epithelial cell fraction to 69% of the untreated left cheek pouch, which was significant by t-test (p=0.0001), Duncan's or Tukey's test.

These data are consistent with the hypothesis that topically applied Transforming Growth Factor Beta may act by temporarily arresting or delaying progression of oral epithelium into S-phase. This concept is consistent with previous results in which hematopoietic progenitor cells treated with TGF-β3 accumulated in the Gl phase of the cell cycle (Strife et al., 1990) and were similarly protected from chemotherapeutic agents in vitro (Lemoli et al., 1992) or in vivo. In contrast, most epithelial or hematopoietic-derived malignancies are relatively refractory to growth inhibition by TGF-β and are apparently compromised in the signalling pathways through which TGF-β causes cell cycle arrest in late G1. The low systemic exposure of topically applied TGF-β to intact oral mucosa, coupled with the differential responsiveness of normal and tumor tissue to TGF-β, suggest broad feasibility of such means of chemoprotection in cancer treatment. We do not exclude additional mechanisms by which TGF-β might moderate chemotherapy associated toxicities, such as modulation of receptor or cytokine expression. Similar experiments are performed with TGF-β1, TGF-β32, TGF-β4, and TGF-β5.

TABLE 6

Effect of topical application of Transforming Growth Factor Beta on cell cycling of hamster oral epithelium in vivo.

| Group | LI (±SEM) | BrdU labelling % of control | P-value | PCNA staining % of control | P-value |
|---|---|---|---|---|---|
| control 0 hrs. | 4.2 (±0.3) | — | — | — | — |
| post β3 16 hrs | 1.8 (±0.2) | 44% | 0.0008 | — | — |
| post β3 54 hrs | 2.1 (±0.5) | 51% | 0.09 | 69% | 0.0001 |
| post β3 | 3.8 (±0.4) | 90% | 0.27 | — | — |

Clinical Evaluation and Patient Administration

Based on scheduling data and dosage data derived by modelling in the Golden Syrian hamster as described herein, Phase I trials are conducted to evaluate safety. Little or no human toxicity is expected in acute topical administration of Transforming Growth Factor Beta to the oral cavity. Dose escalation studies and chronic exposure studies may be performed. In Phase II, patients are evaluated for a reduction in the frequency and severity of oral mucositis associated with chemotherapy. In clinical practice, patients are protected from oral mucositis by topical or systemic administration of Transforming Growth Factor Beta in a suitable carrier prior to chemotherapy. Administration of Transforming Growth Factor Beta may be continued for a period after chemotherapy i.e. that period of pharmacologic exposure to ensure protection of the oral tissue from the chemotherapeutic agent. The dose range of Transforming Growth Factor Beta administered to patients is determined first by modelling in the hamster as described herein and then is refined in Phase I/Phase II trials. The amount of Transforming Growth Factor Beta applied to the oral cavity in these range finding studies is determined empirically. The patient is monitored for oral mucositis according to several well established scoring criteria, for example the ECOG (Eastern Cooperative Oncology Group) score for oral mucositis. The dose or schedule of Transforming Growth Factor Beta administered to the cancer patient may be adjusted in subsequent rounds of chemotherapy, according to the extent or duration of oral mucositis in the first round of therapy.

EXAMPLE 7

In Vivo Growth Inhibition of Gastrointestinal Epithelia

The growth inhibitory effects of Transforming Growth Factor Beta on primary normal and neoplastic colon organ cultures was evaluated with a view to establishing Transforming Growth Factor Beta as a chemoprotective agent to reduce gastrointestinal toxicity in the treatment of patients with chemotherapeutic drugs.

Proliferation of colon cells in various stages of differentiation is measured by the incorporation of either [$^3$H]-thymidine or bromodeoxyuridine (BrdU) into colon biopsy organ cultures followed by sectioning and staining of the intact crypt. A 1 mm biopsy specimen is gently washed in DMEM, 10% FCS, 37° C. Three micron sections are cut to avoid unequal distribution of radiolabel. Incubation with TGF-β3 at 0.1 pM, 10 pM, 1 nM, 100 nM and 10 μM is carried out over several time points.

Colon specimens are labeled in 2 ml of DMEM+10%, 37° C. equilibrated in a 5% $CO_2$ incubator, containing 1 $\mu$Ci/ml [3H]-thymidine (20 $\mu$Ci/mmole) or 400 $\mu$M BrdU for 1 hour. Sections are washed, fixed in 10% formalin, embedded and cut longitudinally to expose the morphology of the colon crypt. Tissue sections are coated with liquid emulsion and autoradiographed.

The proliferation index of cells in various stages of crypt development is determined by microscopic counting of exposed silver grains. Routinely, cells with >4 grains score as positive. Similarly cells labelled with anti-BrdU antibodies are counted as a percentage of the total number of cells. In normal tissue, only the lower third of the crypt (containing the stem cell population) are labeled. Adjacent tissue serves as an internal control. The appearance of differentiation markers on colon crypt cells are monitored using available monoclonal antibodies to cytokeritins and colon specific antigen (fetal). Alternatively, cellularity of the villus and crypt may be used a over a period of 4 days as a marker of cell proliferation.

To establish in vitro models for the chemoprotective effects of Transforming Growth Factor Beta, doses of cytotoxic drug in organ culture or in dispersed mixed cell culture required for toxicity are assessed. Organ cultures are prepared as described previously (Shamsuddin, 1990) Parallel cultures are incubated in a range of 5-FU concentrations and proliferation measured by [3H]-thymidine incorporation and sectional autoradiography. To establish dispersed, mixed cell colon cultures, biopsy material are cut to >0.5 $cm^2$, washed in phosphate buffered saline (PBS), finely titrated, centrifuged, rinsed, washed (5×) and cultured in a mixture of Leibowitz's medium L15 and suspension modified MEM (SMEM) with a final $Ca^{+2}$ concentration of 0.5mM, 10% fetal calf serum, 100 units penicillin, 50 $\mu$g/ml streptomycin, 25 $\mu$g/ml gentamicin, 2 mM glutamine, 1 ng/ml epidermal growth factor (EGF), 20 $\mu$g/ml insulin, 10 $\mu$g/ml transferrin, 25 nM sodium selenite and grown on collagen (Type I) coated culture plates (Wong et al., 1975, Moyer et al.,1990). Colon cells grown on collagen coated coverslips in a range of 5-FU concentrations are incubated in [3H]-thymidine (0.2 $\mu$Ci/ml) for thirty minutes, washed and chased overnight in fresh media. Cells are washed, fixed/stained, coverslips dipped in liquid photographic emulsion and autoradiographed. Proliferation is measured by counting exposed silver grains. Chemoprotection by Transforming Growth Factor Beta in vitro is measured by pre-addition of a range of Transforming Growth Factor Beta doses to colon organ or cell cultures followed by 5-FU at or near the toxic dose, and [3H]-thymidine labelling at intervals after exposure to cytotoxic drug as a measure of cellular recovery.

The effective dose for systemic administration of Transforming Growth Factor Beta for gastrointestinal protection may be determined by animal modelling in mice. Histomorphic analysis of representative cross sections of small intestine at defined distances between the pylorus and the caecum are performed. Serial hematoxylin-eosin stained transverse sections of duodenum, jejunum and ilium were measured for numbers of crypts and villi per transverse section. The number of epithelial cells per representative villus section and the number of cells per representative crypt section are constant in the steady state and the rate of renewal is determined by the number of mitotic figures per representative crypt section. Kinetic analysis is obtained by autoradiography following $^3$H-thymidine or BrdU labelling in vivo (25 $\mu$Ci $^3$H-thymidine/mouse or 5 mg BrdU/mouse). The labelling index of the tissue section provides a standard measure of the proliferation status of that tissue and demonstrates that Transforming Growth Factor Beta reversibly inhibits proliferation of the gastrointestinal epithelia.

Also, the proliferation of the gastrointestinal epithelia is assessed by measurement of villus and crypt cellularity, and villus height. Specifically, the small intestine is removed and the lumen flushed with cold (4° C.) HBSS, the tissue is then briefly blotted dry and weighed. After fixation in Carnoy's fluid for 3 h, three segments (approx. 10% each of the total length) are removed from the proximal (duodenum), middle (ileum) and distal (ileum) regions of the small intestine, embedded in wax and cut as TS sections (4 $\mu$m thickness). Sections are stained with Hematoxylin and Eosin or PAS/ Alcian blue (Goblet cells and mucins). Measurements are made of wet tissue weights; TS diameter of the intestine ($\mu$m, 10 measurements per animal); relative crypt: villus ratio (total number of crypts and villi per circumference—5 sections of gut per animal); crypt height in $\mu$m (measured from the base to the top of the crypt only in centrally sectioned crypts where there is an open lumen from the base of the top of the crypt, 20 measurements per animal); villus height (measured in $\mu$m from the crypt: villus junction to the villus tip, 20 measurements per animal; and the crypt cellularity (the number of epithelial nuclei measured from the base to the top of the crypt, but only in centrally sectioned crypts, 20 measurements per animal). These data allow determination of the preferred dose, schedule and route of administration for Transforming Growth Factor Beta mediated cell cycle inhibition.

In a typical experiment with Balb/c mice, all of the animals received two intravenous injections of 5-fluorouracil (5-FU) at 150 mg/kg body weight separated by seven days. Control mice were sacrificed one day after receiving the second intravenous 5-FU injection. TGF-β3 treated animals received four intraperitoneal (IP) injections of TGF-β3 (2 $\mu$g per injection) around the time of the first 5-FU injection, five (IP) injections of TGF-β3 (2 $\mu$g per injection) around the time of the second 5-FU injection and sacrificed one day following the second 5-FU injection. The first IP administrations of TGF-β3 were at 24 hours and 3 hours preceding, at the time of, and 3 hours following the first intravenous 5-FU injection. The second administrations of TGF-β3 were at 29 hours, 24 hours, and 3 hours preceding, at the time of, and 3 hours following the second 5-FU injection. Mice were sacrificed by cervical dislocation and the small intestine removed and immediately placed in a phosphate buffered solution of 10% formalin (PBSF) at room temperature. The lumen was flushed with PBSF and the small intestine cut into three equal segments as above. From each animal, five samples of 3 mm in length were cut from the length of each segment, transferred and stored in 5 ml of PBSF. The samples were embedded in wax and transverse sections 5 $\mu$m in thickness were cut. The cut sections were transferred to slides and stained and measured as above.

As presented in Table 7, the length of the villus and crypt from the animal receiving TGF-β3 was significantly longer than was noted in the animal receiving only the two injections of 5-FU. The crypt cellularity in the TGF-β3 treated animal was also greater than the animal that did not receive TGF-β3. Measurements were made from each section of the number of cells in the crypt, the number of cells in the villus, the extent of apoptosis, villus height (in $\mu$m from the crypt:villus junction) to the villus tip.

Similar experiments are performed with TGF-β1, TGF-β2, TGF-β4, and TGF-β5.

TABLE 7

| Group | Section | Villus (μm) | Crypt (μm) | Crypt Cellularity |
|---|---|---|---|---|
| Control | Duodenum | 15 | 5 | ND |
| | Jejunum | 25 | 5 | 7 |
| | Ileum | 20 | 5 | 12 |
| With TGF-β3 | Duodenum | 55 | 5 | 20 |
| | Jejunum | 35 | 10 | 15 |
| | Ileum | 30 | 10 | 20 |

ND = Not Determined

In another experiment this time with BDF-1 mice, all of the mice received two intravenous injections of 5-fluorouracil (5-FU) at 150 mg/kg body weight separated by four days. Control animals were sacrificed one, two, four and seven days following the second intravenous 5-FU injection. TGF-β3 treated animals received three intraperitoneal (IP) injections of TGF-β3 (5 μg per injection) around the time of the second 5-FU injection and sacrificed one, two, four and seven days after receiving the second 5-FU injection. The IP administrations of 5 μg TGF-β3 were at 6 hours and 3 hours preceding and at the time of the second intravenous 5-FU injection. Mice were sacrificed by cervical dislocation and the small intestine removed and immediately treated as above.

As shown in FIGS. 10A–10D, the sections taken from the BDF-1 animal sacrificed four days following the second intravenous 5-FU injection and receiving Transforming Growth Factor Beta showed significantly greater number of villi and overall cellularity when compared with sections taken from an animal receiving only the two injections of 5-FU. Measurements were made from each section of the number of cells in the crypt, the number of cells in the villus, the extent of apoptosis, villus height (in μm from the crypt:villus junction) to the villus tip.

In a third experiment, Balb/c mice received two intravenous injections of 5-fluorouracil (5-FU) at 150 mg/kg body weight separated by seven days. Control animals were sacrificed one, two, four and seven days following the second intravenous 5-FU injection. Transforming Growth Factor Beta treated animals received 3 intraperitoneal (IP) injections of TGF-β3 in a similar manner to the BDF mice above. The mice were sacrificed and the intestine prepared as above.

As shown in FIG. 11A–11F, the sections taken from the Balb/c animal sacrificed four days following the second intravenous 5-FU injection and receiving TGF-β3 shows significantly greater number of villi and overall cellularity when compared with sections taken from an animal receiving the two injections of 5-FU without TGF-β3. Measurements were made from each section of the number of cells in the crypt, the number of cells in the villus, the extent of apoptosis, villus height (in μm from the crypt:villus junction) to the villus tip. Thus, Transforming Growth Factor Beta increases crypt cellularity and villus length and prevents chemo- induced apoptosis.

Similar experiments are performed using TGF-β1, TGF-β2, TGF-β4, and TGF-β5 for in vivo growth inhibition of gastrointestinal epithelia.

EXAMPLE 7

Use of Transforming Growth Factor Beta in Protection of the Crypts of the GI Tract from Irradiation After irradiation of the G.I. tract some undamaged crypt-base cells may be capable of regenerating crypts via clonal growth. Destruction of all clonogenic cells in a crypt results in loss of that crypt within about 48 hrs. If sufficient crypts are lost the integrity of the mucosal liningis threatened, particularly in the region of the villus. Breakdown in this integrity results in a loss of barrier function and the symptoms of the GI syndrome ensue, which can result in death within the period 3–7 days post-irradiation. The dose that causes death in 50% of the mice within 7 days for conventionally housed BDF1 mice, the LD50/7, is about 11.1 Gy.

As described below, administration of Transforming growth factor B protects against crypt loss from irradiation and thus ameliorates the severity of the GI syndrome which ensues.

TGF-β3 was shown to protect intestinal crypt cells from irradiation induced damage. Mice were injected (ip) with TGF-β3 (2.5 μg) at −24, −8, −4 and 0 hours (Group B), or −4, −3, −2, −1 and 0 hours (Group D) prior to irradiation at 1200 rads at time 0. Control groups (A and C) received saline injections in place of TGF-β3. Administration of TGF-β3 by both schedules enhanced survival of crypt cells in the gut.

TABLE 8

TGF-β3 CRYPT SURVIVAL (CLONOGENIC OR STEM CELL SURVIVAL)

| | | Surviving crypts/ circumference at 3 days | |
|---|---|---|---|
| Group A | −24 H, −8, −4, 0 Saline injections | 37.3 | Control |
| Group B | −24 H, −8, −4, 0 TGF-β3 (2.5 μg) 1200 rads | 48.8 | 31% Protection |
| Group C | −4 H, −3, −2, −1, 0 Saline injections | 38.2 | Control |
| Group D | −4 H, −3, −2, −1, 0 TGF-β3 (2.5 μg) 1200 rads | 50.9 | 33% Protection |

Similar experiments are performed using TGF-β1, TGF-β2, TGF-β4, and TGF-β5 for in vivo growth inhibition of gastrointestinal epithelia.

EXAMPLE 8

A Method for Prevention of Effluvium or Alopecia Associated with Chemotherapy.

A common side effect of cytotoxic chemotherapy in the treatment of cancer is a thinning or complete loss of hair (effluvium or alopecia respectively). This side effect of cancer therapy is most common in patients receiving doxorubicin, but may also be observed in patients receiving methotrexate, cyclophosphamide, 5-fluorouracil, vincristine and other chemotherapeutic agents. This toxicity to the growing hair follicle is dose dependent. Approximately 85–95% of hair follicles are actively growing, resulting in scalp hair growth of ~0.3 mm/day. Loss of hair during chemotherapy is psychologically distressful and has provoked some patients to discontinue therapy. The ability of Transforming Growth Factor Beta to inhibit cell cycling of many epithelial cell types is useful in reversibly slowing or blocking cycling of the hair follicle, thereby preventing chemotherapy associated hair loss.

Several animals models have been developed for alopecia, in species where hair growth is asynchronous, as in humans. Species employed include the guinea pig and the Angora rabbit (Powis and Kooistra, 1987). The rabbit model is preferred. Rabbits are given 2 mg/kg doxorubicin, intravenously, twice a week for three weeks. Weekly measurements are made of: i) hair length; ii) shaved hair weight (obtained by shaving a 4×6 cm flank patch); iii) groomed hair weight (obtained by brushing); and iv) body weight. Transforming Growth Factor Beta is administered at a concentration of 1 μg/kg to 250 μg/kg, intraperitoneally, twice daily for up to three days prior to chemotherapy and may continue for up to 2 days after chemotherapy. Alternatively, Transforming Growth Factor Beta may be administered topically to the flank of the rabbit in a concentration range of 10 ng/cm$^2$ to 1000 μg/cm$^2$, twice daily for up to three days prior to chemotherapy and may continue for up to 2 days after chemotherapy. Protection by Transforming Growth Factor Beta of chemotherapy associated hair loss is shown by increased hair length, increased shaved hair weight and increased groomed hair weight.

Based on animal modelling data, patients receiving chemotherapy may be administered Transforming Growth Factor Beta either systemically by intravenous injection at a concentration of 1 μg/kg to 250 μg/kg, and twice daily for up to three days prior to chemotherapy and may continue for up to 2 days after chemotherapy. Alternatively, Transforming Growth Factor Beta may be administered topically to the scalp in a concentration range of 10 ng/cm2 to 1000 μg/cm2, twice daily for up to three days prior to chemotherapy and may continue for up to 2 days after chemotherapy. Transforming Growth Factor Beta may also be used to increase new blood vessel formation in the scalp by a transdermal delivery system or by subdermal application using suitable penetration enhancers or by subcutaneous injection or other appropriate routes which will be recognized by those of skill in the art.

EXAMPLE 9

Transforming Growth Factor Beta in vivo: Chemoprotection of Bone Marrow Cells

The effects of TGF-β3 on the murine hematopoietic system have been investigated in vivo and in vitro. Chemoprotection of bone marrow stem cells in vitro may be shown by the following method. The hematopoietic stem cells of Balb/C mice may be induced to cycle by treatment with 5-FU (150 mg/kg). After four days the bone marrow is removed and treated with TGF-β3 and a chemotherapeutic agent including but not limited to doxorubicin, Ara-C, 5-FU, daunorubicin, methotrexate, vinblastine, vincristine and cyclophosphamide or with chemotherapy agent alone. Chemoprotection by TGF-β3 is measured by culturing the so treated marrow cells in the presence of early acting cytokines (for example kit ligand, IL-1, IL-3) or conditioned medias which support the proliferation of primitive, pluripotent stem cells (for example Mo cell conditioned media). Protected cells will proliferate to form large colonies characteristic of self-renewing pluripotent stem cells. The measure of protection is the increased number of high proliferative potential (HPP) colonies in the TGF-β3 treated versus the untreated marrow. Low proliferative potential (LPP) colonies are smaller more committed hematopoeitic cells. An example of data obtained with in vitro chemoprotection is below:

TABLE 9A

In Vitro TGF-β3 Chemoprotection of 5FU Enriched Mouse Marrow

|  | HPP/LPP | Percent of Control |
| --- | --- | --- |
| Control | 687/9983 | 100%/100% |
| TGF-β3 only | 81/694 | 11.8%/6.9% |
| Ara C only | 1/7 | 0.14%/0.07% |
| TGF-β3 and Ara C | 26/158 | 3.8%/1.6% |

Chemoprotection by TGF-β3 in vivo is shown by the following method. Balb/IC mice are exposed to a cytotoxic agent (typically 5-FU or ara-C) to induce the pluripotent HPP stem cells into cell cycle. After a suitable time period (usually 4 days) a second dose of cytotoxic agent is administered to the animal. Prior to the second dose of cytotoxic agent, TGF-β3 is administered to the animal for a suitable time (generally 2 μg, twice daily for one to three days). A suitable time after the second dose of cytotoxic agent is administered (generally 2 to 4 days), stem cell number and proliferative status is measured. In Transforming Growth Factor Beta treated mice, increased numbers of stem cells are present following chemotherapy (for example 5-FU or ara-C) compared with untreated mice. Similarly, in vivo chemoprotection of marrow stem cells may be observed by the following protocol. TGF-β3 (2 μg, intraperitoneal) is administered to Balb/C mice 4 hours prior to 5-FU (IV, 150 mg/kg) and TGF-β3 treatment continued (2 μg, intraperitoneal) at the time of injection, 4 hours post 5-FU and 20 hours post 5-FU. Marrow is isolated, cultured and stem cell number quantitated. Treatment with Transforming Growth Factor Beta results in a four fold greater number of surviving stem cells with which to reconstitute the blood system. Transplantation of lethally irradiated Balb/C mice (850 rads) with Transforming Growth Factor Beta protected stem cells can either fully reconstitute or lead to significantly increased life spans of transplanted mice, depending on the protocol employed. In an additional example, six Balb/c mice received two intravenous injections of 5-fluorouracil (5-FU) separated by four days. The first injection of 5-FU was at 150 mg/kg and the second injection of 5-FU was at 130 mg/kg. Three control mice were sacrificed one day after receiving the second intravenous 5-FU injection. Three TGF-β3 treated animals received three intraperitoneal (IP) injections of TGF-β3 (2 μg per injection). The three IP administrations of 2 μg TGF-β3 each were at 6 hours and 3 hours preceding and at the time of the second intravenous 5-FU injection. All mice were sacrificed by cervical dislocation, femoral bone marrow removed and colony forming cells assayed using a double-layer agarose system. Sixty-millimeter petri dishes containing a 2-ml underlayer consisting of culture media, cytokines and 0.5% agarose were overlayed with 1 ml of BM cells suspended in culture media containing 0.36% agarose. The final concentration of cytokines in the double-layer were 10% WEHI-3-conditioned medium (Shieh, J.-H. et al., 1991) (as a source of murine IL-3), 100 U/ml IL-1β and 1000 U/ml mGM-CSF. The cell concentration in the 1 ml cell layer was 1×10$^5$ cells. Double layer cultures were grown for 10 days at 370° C. under low oxygen tension (5%$O_2$/5%$CO_2$/90%$N_2$). Each 60 mm plate was either fixed with 2 ml of 0.5% glutaraldehyde in PBS or stained with 2 ml of a solution of iodonitrotetrazolium (INT) (1 mg/ml) and scored for colony formation. HPP and LPP colony classifications were as previously described (Moore, et al., 1987).

TABLE 9B

In Vivo Chemoprotection of Bone Marrow Cells by Transforming Growth Factor Beta

| | Average colonies per mouse | | |
|---|---|---|---|
| | HPP | LPP | TOTAL |
| Control Unprotected | 542 | 2396 | 2938 |
| TGF-β3 Chemoprotected | 949 | 4129 | 5079 |

In a similar manner, experiments are performed with TGF-β1, TGF-β2, TGF-β4, and TGF-β5.

Treatment of patients with Transforming Growth Factor prior to multicycle cytotoxic chemotherapy, will protect against hematopoietic stem cell loss and thereby reduce the incidence of febrile neutropenia, the number of patient hospital days, reduce the use of antibiotics, and allow successful completion of chemotherapy.

EXAMPLE 10

Transforming Growth Factor Beta In Vivo: Effects on Survival without Cytokines and Synergy with Cytokines

Several strategies can be employed for in vivo administration of TGF-β3 as a hematopoietic chemoprotectant. TGF-β3 is used during or immediately prior to chemotherapy to protect the early hematopoietic stem cell population in multicycle or accelerated cycle chemotherapy. Hematopoietic growth factors can be successfully used in the recovery from myelosuppression. Prevention of long term stem cell depletion, neutropenia and continued tolerance to further chemotherapy are clinical endpoints measured in trial.

(a) Protection from the effects of 5-FU in the absence of cytokines: Two groups of Balb/c mice were treated with 150 mg/kg 5-FU administered i.v. on day zero followed by 130 mg/kg on day 4. The TGF-β3 treated group received five doses of 2 μg TGF-β3 each in PBS administered by injection i.p. The first dose was given on day 3 and the remaining four doses were given 3 hours prior to, coincident with, 3 hours after and one day after the second 5-FU treatment. Control animals received injections of PBS alone.

The survival results on day 9 were as follows:

| | Survival |
|---|---|
| TGF-β3 treated group | 40% |
| Control Group | 0% |

These results demonstrate that TGF-β3 is capable of enhancing survival of 5-FU treated mice in the absence of exogenously added cytokines.

Figure 12A:
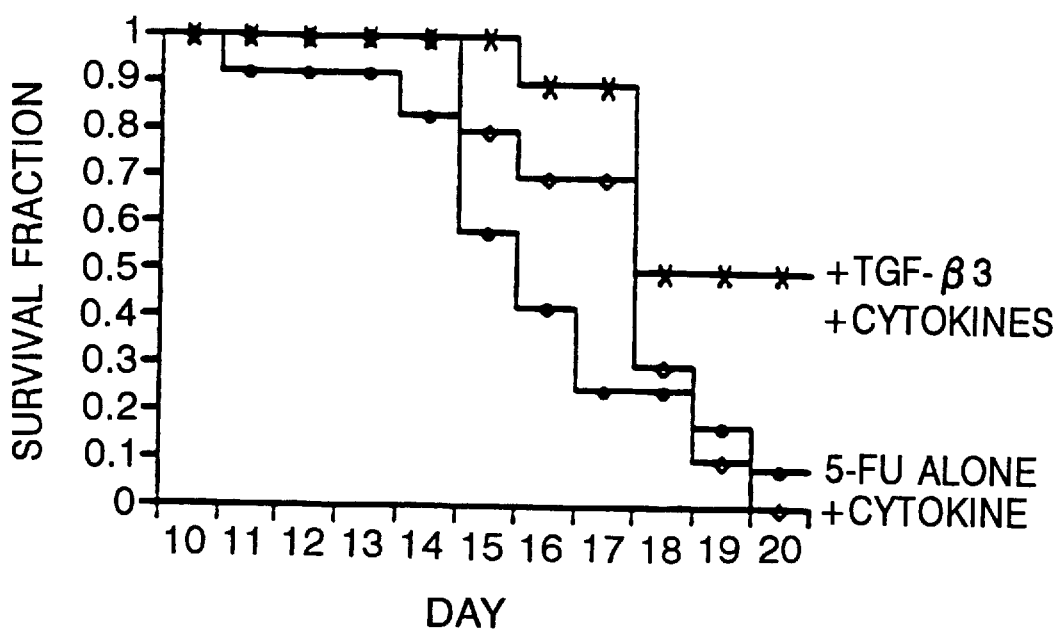

(b) Protection from the effects of 5-FU in the presence of exogenously administered cytokines:

For example, Balb/C mice were treated with two cycles of 5-FU (150 mg/kg) spaced seven days apart, which is normally a lethal course of chemotherapy in these animals. TGF-β3 administration significantly increased survival time ($p=0.0009$). Percent survival is shown for day 26 post 5-FU (FIG. 12A).

| 2 × 5-FU [n = 12] | 8% survival |
|---|---|
| 2 × 5-FU + cytokine rescue [n = 10] | 0% |
| 2 × 5-FU + TGF-β3 (3 × 2 μg; 6 hrs.) + cytokine rescue [n = 5] | 50% |
| 2 × 5-FU + TGF-β3 (4 × 2 μg; 24 hrs.) + cytokine rescue [n = 10] | 50% |
| 2 × 5-FU + TGF-β3 (6 × 2 μg; 30 hrs.) + cytokine rescue [n = 5] | 15% |

FIG. 12B shows weight retention data for the same experiment. Note that very high doses of TGF-β3 and 5-FU accelerates weight loss and mortality.

A similar survival study also showed increased survival and weight retention in TGF-β3 treated mice (day 17 post 5-FU; (FIG. 12C):

| 2 × 5-FU | 0% survival |
|---|---|
| 2 × 5-FU + cytokine rescue (G-CSF + IL-1) | 20% |
| 2 × 5-FU + TGF-β3 (5 × 2 μg; 27 hrs.) + cytokines | 80% |

Alternatively, hematopoietic growth factors (eg. kit ligand) may be administered before chemotherapy to increase total bone marrow cellularity and increase the number of hematopoietic cells surviving cytotoxic chemotherapy. Expanding the hematopoietic stem cell population using growth factors requires a mechanism to restore these cycling cells back to a non-dividing state prior to chemotherapy. TGF-β is unique in its ability to perform this function. TGF-β3 is used to protect this expanded population of hematopoietic stem cells prior to chemotherapy and the increased reserve of the more mature hematopoietic cells reduces the fall in white blood cell count associated with chemotherapy.

For example we have shown TGF-β3 can protect BDF1 mice from the lethal effects of stem cell factor (SCF) and chemotherapy (5-FU). In this model SCF is administered prior to 5-FU treatment to deplete the stem cell population. As shown below this SCF/5-FU combination is lethal and is used here to measure TGF-β3 mediated stem cell chemoprotection. Two cycles of 5-FU, SCF and TGF-β3 treatment were used, spaced 7 days apart. Day 17 survival data and day 10 blood cell counts (WBC) are shown (Table 10).

TABLE 10

| Treatment | Survival | WBC ($10^6$) |
|---|---|---|
| 5-FU (n = 10) | 100% | 12.6 |
| 5-FU + TGF-β3 (n = 10) | 100% | 15.9 |
| 5-FU + SCF (n = 10) | 0% | 6.0 |
| 5-FU + TGF-β3 + SCF (n = 10) | 40% | 6.1 |

Similar in vivo experiments are performed using TGF-β1, TGF-β2, TGF-β4, and TGF-β5.

EXAMPLE 11

Acute Toxicology and Chemoprotection of Normal Mice

Acute administration of escalating doses of Transforming Growth Factor Beta can be investigated for toxicity (survival, weight loss) in normal Balb/c or BDF1 mice. Various hematologic parameters, progenitor cell assays and immune function assays are undertaken. The status of the hematopoietic stem cell compartment (total numbers in marrow, spleen and circulation, and cell cycle status) is determined using the in vivo CFU-S assay, and the in vitro CFU-GEMM and high proliferative potential (HPP) CFU assays.

Progenitor cells for the erythroid (BFU-E, CFU-E), myeloid (CFU-GM, CFU-M, CFU-G) and megakaryocyte/platelet series (CFU-MK) are assayed. Lymphoid function is measured by B-and pre B-lymphocyte colony assays, etc. Subsets of myeloid and lymphoid cells in tissues is determined by FACS analysis using lineage-specific monoclonal antibodies. White blood cells (WBC), platelets, red blood cells (RBC) and hematocrit are measured in repeated tail vein blood samples. Serum samples are obtained and are assayed for TGF-$\beta$3, G-CSF, GM-CSF, M-CSF, IL-1,3,4,5 and TNF by bioassay and radioimmunoassay. Neutrophil function assays include in vivo and in vitro chemotaxis, bactericidal capacity and receptor expression for multiple cytokines.

The ability of Transforming Growth Factor Beta to protect hematopoietic stem cells from the cytotoxic effects of chemotherapeutic agents is assessed in animal models. Untreated BALB/c mice, or groups pre-treated with Transforming Growth Factor Beta, receive a single i.v. dose of 5-FU (150 mg/kg). In subsequent experiments cyclophosphamide (200 mg/kg), vinblastine (2.5 mg/kg), adriamycin (2.5 mg/kg) or methotrexate (150 mg/kg) is employed. The number of peripheral circulating blood cells and the various hematopoietic progenitor cells are determined, including CFU-S, CFU-GM, HPP-CFU-C, BFU-E, CFU-Mk and CFU-GEMM.

It is preferable, although not necessary, to identify the optimal parameters of dosage and scheduling relationships by the experiments hereinabove, i.e. Transforming Growth Factor Beta is tested in this model. Most of the planned studies are performed using first generation syngeneic transplants of spontaneous breast tumors. In addition to determination of life span, the effect of therapy is determined on tumor growth rate, on partial and complete regression, and on spontaneous metastasis (determined histologically or by tissue retransplantation). Transforming Growth Factor Beta is tested for its ability to mediate a reversible cytostatic block on hematopoietic progenitor and stem cell proliferation, conferring resistance to toxicity or chemotherapy.

Similar in vivo experiments are performed using TGF-$\beta$1, TGF-$\beta$2, TGF-$\beta$4, and TGF-5.

EXAMPLE 12

Chemoprotection of Primary Human Bone Marrow and Peripheral Blood Samples

Primary human bone marrow and peripheral blood samples were evaluated for the growth of the different hematopoietic lineages in the presence and absence of exogenous Transforming Growth Factor Beta. Stem cell cultures were purged of mature, well differentiated cells. Specifically, buffy coat cells were collected by centrifugation (800 rpm, 10', 5° C.), suspended in McCoy's medium including 10% heat inactivated FCS ('complete medium'). Platelets were removed by Percoll gradient centrifugation (1.050 g/ml; Pharmacia) and a low density, small primitive cell population obtained after re-centrifugation on a Perooll gradient (1.075 g/ml). individual populations of B- and T-lymphocytes, granulocytes, monocytes and more differentiated erythroid populations can be immunodepleted (centrella et al., 1986) by panning $2 \times 10^8$ light-density cells with monoclonal antibodies (anti-B1, anti-B4, anti-LyT3, anti-My4, anti-My8, anti-903, anti-N901, anti-Leul and anti-glycophorin A (R10) and WEM-G11) directed against mature cell surface apitopes for 30 minutes on ice cells were washed twice in cold complete medium and assayed for progenitor Cells (Strife et al., 1988, Strife, 1987). The primitive stem cell population were grown in methylcellulose support (Iscove's modified Dulbecco's medium (IMDM; Gibco), 24% PCS, 0.8% dialyzed bovine serum albumin, 100 $\mu$M $\beta$-mercaptoethanol, and 1.3 methylcellulose in 35 mm Lux culture plates) in the presence of 10 pM, 100 pM and 1000 pM TGF-$\beta$3 with and without Mo T-lymphocyte conditioned media, a source of colony stimulating factors (Golde, D. W. et al., 1980) in quadruplicate cultures maintained in 5% $CO_2$.

Figure 13:
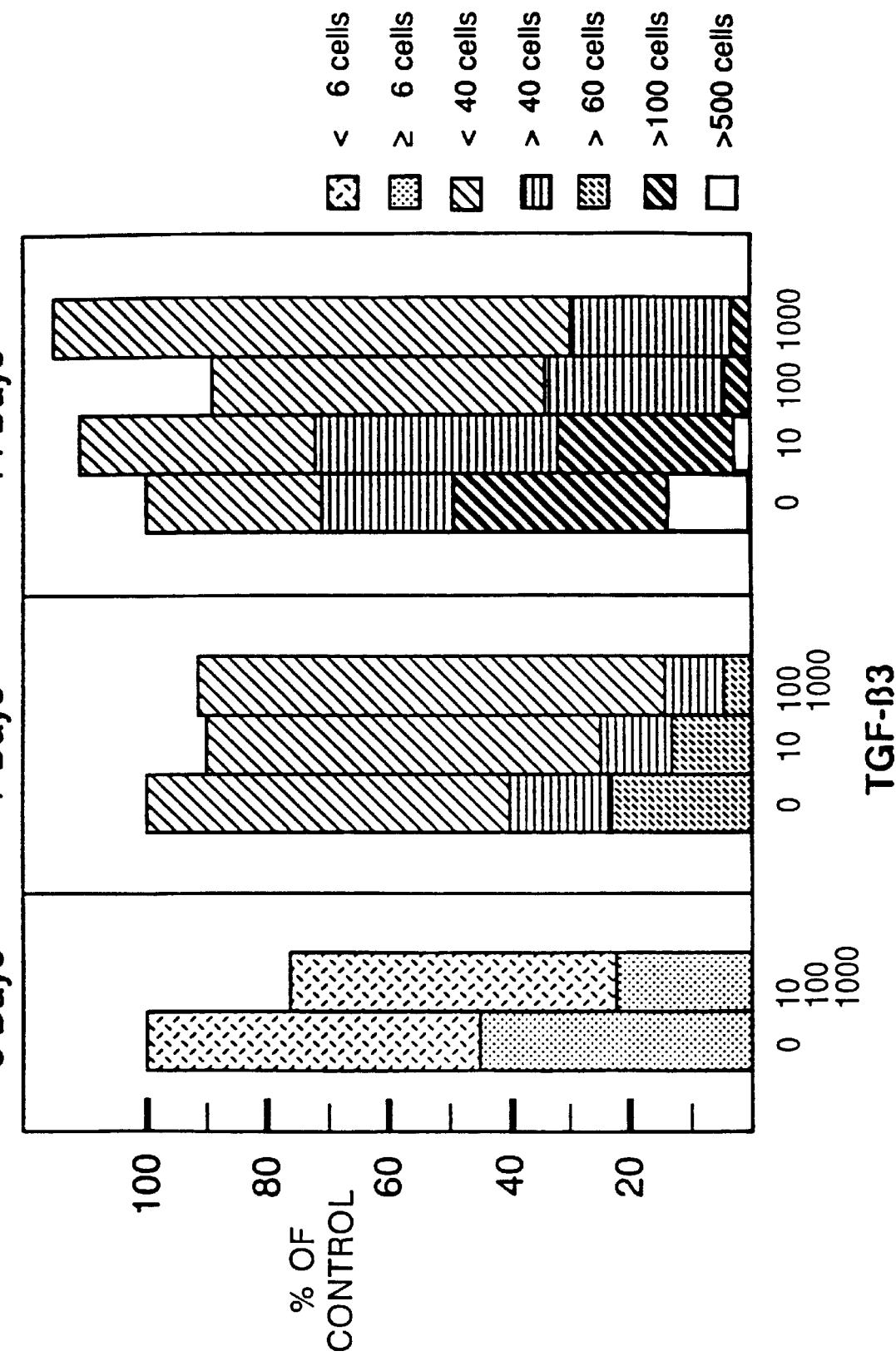
FIG. 13: Inhibition of hematopoietic stem cells by Transforming Growth Factor Beta. Primary bone marrow cells were enriched for a progenitor stem cell population by immunodepletion and cultured as described. Cells were grown in the presence of Mo-T Cell conditioned media and increasing concentrations of purified TGF-$\beta$3 (0, 10, 100, 1000 pM) and colony sizes determined at 3, 7 and 14 days. TGF-$\beta$3 inhibited proliferation and subsequent increase in hematopoietic colony size in a dose and time dependent manner.

Colony forming units of the various hematopoietic lineages were counted microscopically at 3, 7, 14 and 21 days. An example of this experiment is shown in FIG. 13. Individual colonies were aspirated onto glass slides, selectively stained with May-Grunewald-Giemsa and the presence of neutrophils, monocytes or eosinophils observed. These experiments allow one skilled in the art to determine if the growth inhibitory action of Transforming Growth Factor Beta is lineage-specific at given doses of Transforming Growth Factor Beta, determine the time course of inhibition and determine the dose of Transforming Growth Factor Beta required for inhibition of a given cell type.

Figure 14:
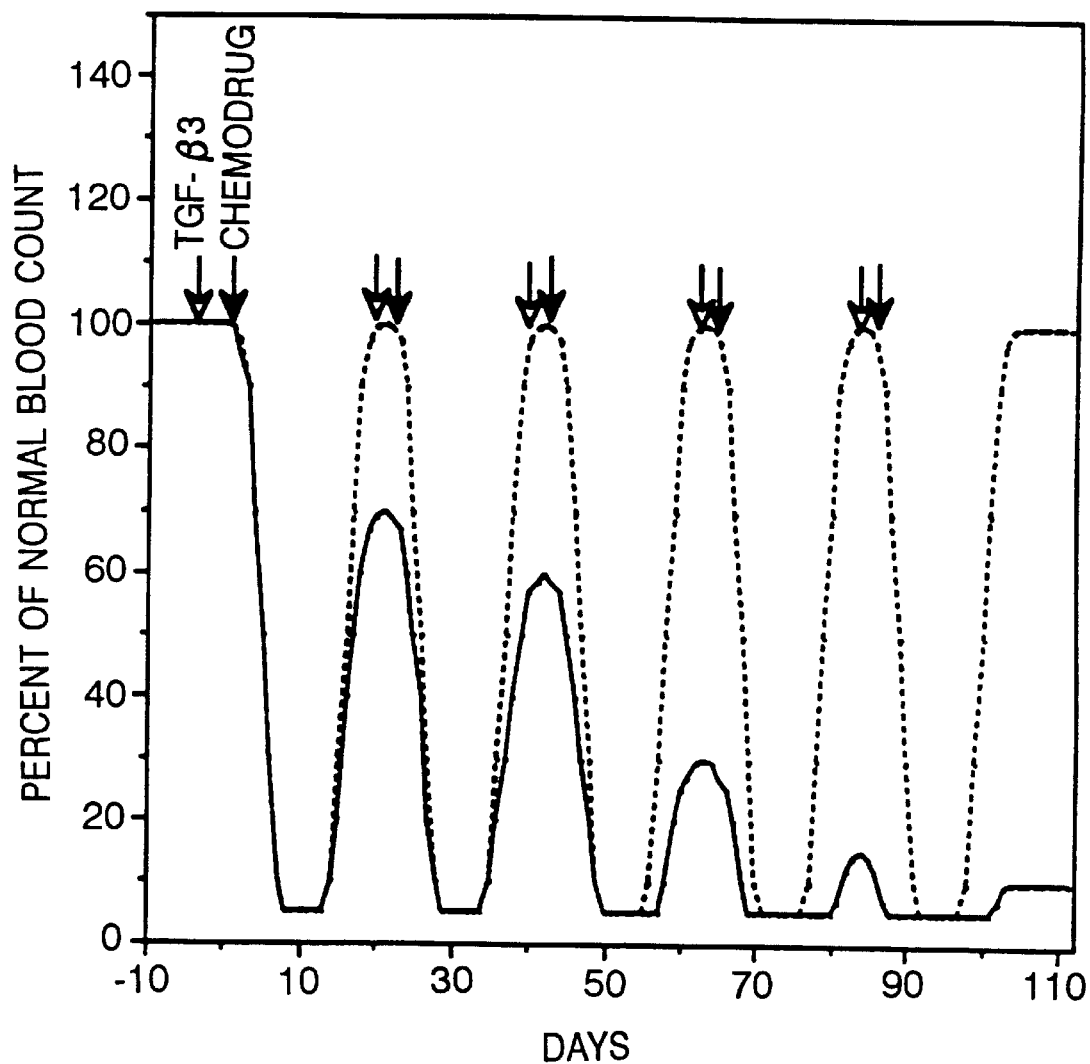
FIG. 14.

FIG. 14 shows a theoretical plot of TGF-$\beta$3 chemoprotection to reduce chemotherapy-induced reduction of normal blood count. As a general rule, the smaller hematopoietic precursors represent more primitive progenitor stem cells while the larger cells are usually more mature, as analyzed by the appearance of maturation-specific cell surface epitopes. Enriched progenitor populations obtained by immuno-depletion as described may be size selected by Percoll gradient centrifugation and different size cell populations evaluated for specific lineages in combinations of Mo conditioned media and TGF-$\beta$3 at 3, 7, 14 and 21 days. Assays for early stem cell populations (HPP-CFU of CFU-A), progenitor cells (CFU-E, CFU-GEMM, BFU-E, CFU-MK), pre-B colony, B colony, T colony, cytolytic T cell, and antigen stimulation assays are currently well developed.

EXAMPLE 13

Use of Transforming Growth Factor Beta in Autologous Bone Marrow Transplantation and syngeneic Mouse Model Autologous bone marrow transplantation is a method in which the bone marrow of a patient is removed prior to chemotherapy to reduce hematopoietic stem cell toxicity. Autologous bone marrow transplantation has also been performed in patients with acute nonlymphocytic leukemia using 4-hydroperoxycyclophosphamide to treat the marrow ex vivo (Cashman, J. D. et al., 1990).

In one instance, Transforming Growth Factor Beta is used to inhibit the proliferation of the bone marrow stem cell population prior to chemotherapy of bone marrow in vivo in patients with blood-bone tumor cells. Briefly, Transforming Growth Factor Beta is contacted with the patient bone marrow at a sufficient concentration to inhibit the normal hematopoietic cells (for example, 1–1000 pM) as determined by one skilled in the art. At a given time after Transforming Growth Factor Beta treatment of bone marrow ex vivo (typically but not limited to 6–24 hours or as determined by the physician) and the tumor cell population refractory to the effects of Transforming Growth Factor Beta, the cells are treated with a cytotoxic chemotherapeutic agent (e.g. adriamycin, 5-fluorouracil, and vinblastine). The treated marrow is returned to the patient at a time determined by the physician and the normal hematopoietic cells allowed to recover from the growth inhibiting effects of Transforming Growth Factor Beta and proliferate, thus reconstituting that component of the patients hematopoietic system.

Alternatively, the bone marrow cells are treated with Transforming Growth Factor Beta as described and the bone marrow cells cultured ex vivo as described such that the leukemic cell population continues to proliferate and terminally differentiate while the normal population is growth arrested. Continued culture in this way results in the terminal growth arrest of the leukemic population and enrichment of the normal cell population. Further, enrichment of the normal cell population may be accelerated by contacting the normal cell population with hematopoietic growth factors, e.g. kit ligand, G-CSF, GM-CSF, M-CSF, IL-1, 2, 3, 4, 5, 6, 7, 8, 9, 10, 11. Bone marrow thus treated is returned to the patient, substantially free of leukemic cells.

A bone marrow transplantation experiment in a syngeneic Balb/C mouse model was performed as follows: TGF-3 (10 ng/ml) treated bone marrow cells taken from donor mice were protected from the cytotoxic effects of Ara-C (100 μg/ml) and this bone marrow population was then-transplanted into lethally irradiated mice, enhancing their long term (greater than 25 day) survival (20% survivors). Control animals transplanted with bone marrow cells which had not been protected by TGF-β3 treatment before Ara-C exposure resulted in no survivors (0% survival).

Similar ex vivo hematopoietic chemoprotection and in vivo transplantation experiments are performed using TGF-β1, TGF-β2, TGF-β4, and TGF-β5.

EXAMPLE 14

Demonstration of Time and Concentration Dependent Chemoprotection by Transforming Growth Factor Beta of Early Hematopoiatic Stem Cells from Ara-C In Vitro.

In this experiment, femoral bone marrow enriched for early hematopoietic progenitors wore taken from Balb/c mice 4 days after receiving a single intravenous injection of 5-fluorouracil (5-FU) at 150 mg/kg body weight. Harvested bone marrow cells (BM) was diluted to $7.5 \times 10^5$ cells/ml with culture media consisting of Iscove's modified Dulbecco's medium with 20% fetal bovine serum (FBS) supplemented with 100 U/ml purified recombinant human IL-1β and 20 ng/ml purified recombinant murine kit ligand (mKL) and 1 ml was added to each well of a 24-well cluster plate. Starting with the beginning of the third day, TGF-β3 was added at 10 ng/ml final concentration at twenty-four, twelve, and zero hours prior to the addition of Ara-C and incubated at 37° C. in a fully humidified 5% $CO_2$ atmosphere. Ara-C at a final concentration of 100 μg/ml was added at the beginning of the fourth day and incubated for an additional 24 hours at 37° C. in a fully humidified 5% $CO_2$ atmosphere. At the end of the incubation, the various treated BM was diluted once (1:10) and washed three times by centrifugation with chilled Dulbecco's phosphate buffered saline containing 10% FBS at 4° C. Colony forming cells were assayed using a double-layer agarose system. Sixty-millimeter petri dishes containing a 2-ml underlayer consisting of culture media, cytokines and 0.5% agarose were overlayed with 1 ml of treated and washed BM cells suspended in culture media containing 0.36% agarose. The final concentration of cytokines in the double-layer was 10% WEHI-3-conditioned medium, as a source of murine IL-3, (Sheih et al., 1991), 100 U/ml IL-1β and 1000 U/ml rmGM-CSF. The cell concentration in the 1 ml of cell layer was $1 \times 10^4$ cells of control cells or $1 \times 10^5$ cells treated with Ara-C, with or without TGF-β3. Double layer cultures were incubated for 9 days at 37° C. under low oxygen tension (5%$O_2$/5%$CO_2$/90%$N_2$). Each 60 mm plate was fixed with 2 ml of 0.5% glutaraldehyde in PBS and scored for colony formation.

Figure 15:
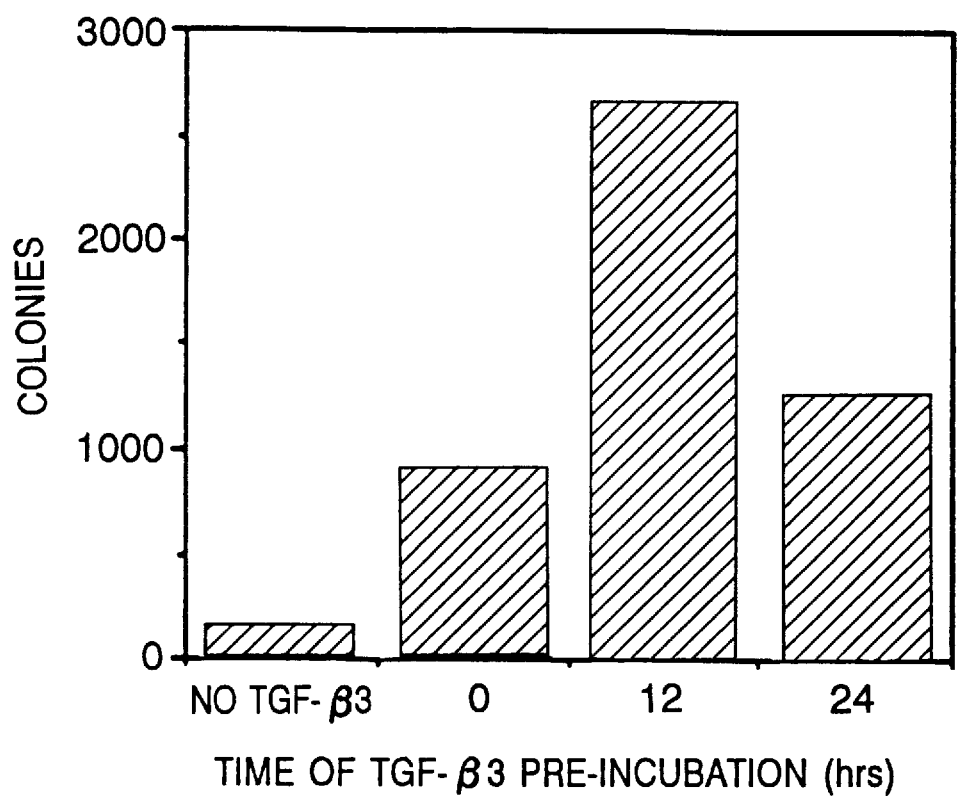
FIG. 15: Demonstration of in vitro time dependence of chemoprotection by TGF-$\beta$3 of early hematopoietic stem cells (HPP-CFU) from Ara-C.

FIG. 15 demonstrates Transforming Growth Factor Beta time-dependent chemoprotection of the early hematopoietic stem cells from the cytotoxic effects of chemotherapeutic agents (i.e. Ara-C). Cells treated simultaneously with TGF-β3 and Ara-C shows significant chemoprotection relative to cells treated with Ara-C only. Longer pretreatment of cells with TGF-β3 (i.e. 12 hrs), prior to exposure with Ara-C, demonstrated a greater level of protection than when cells were treated with TGF-β3 simultaneously with Ara-C. Pretreatment of cells with TGF-β3 24 hrs prior to exposure to Ara-C continues to yield significant chemoprotection. Since TGF-β3 is growth inhibitory, fewer colonies are observed by the group pretreated for 24 hrs with TGF-β3 when compared to the group pretreated for 12 hrs due to the presence of fewer cells at the time of Ara-C exposure and subsequent processing.

Figure 16:
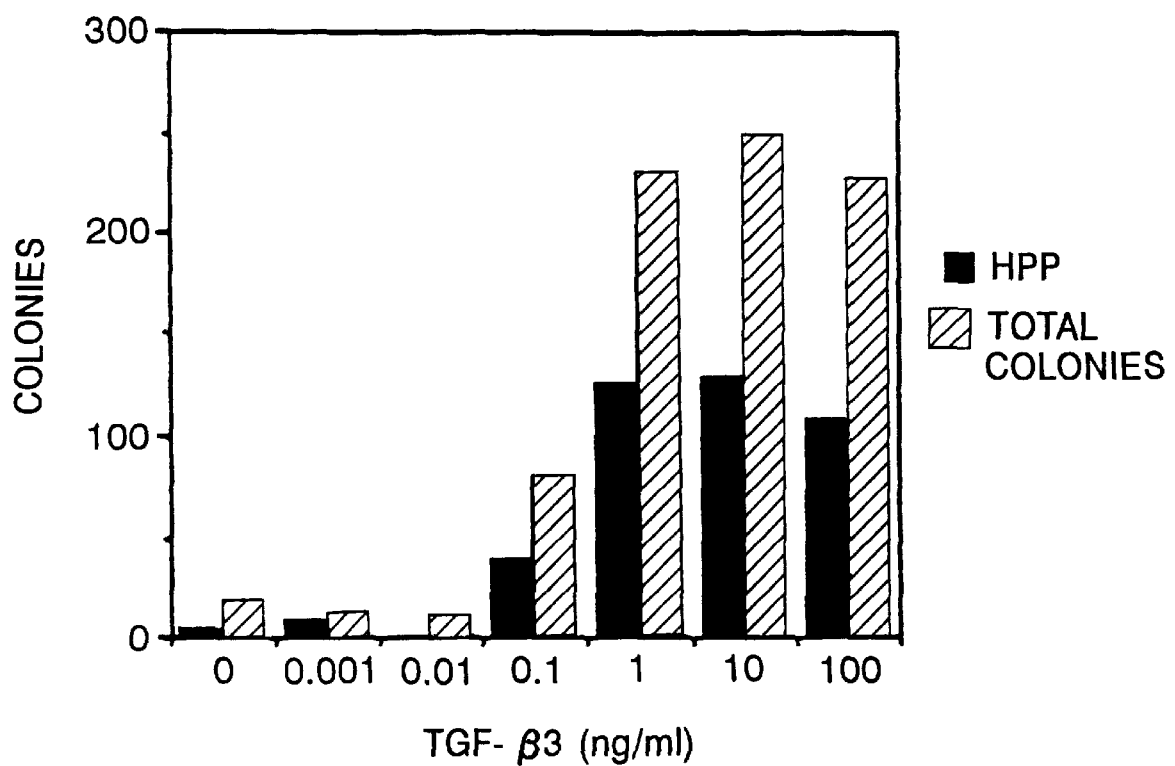
FIG. 16: Demonstration of in vitro concentration dependent chemoprotection by TGF-$\beta$3 of early hematopoietic stem cells (HPP-CFU) from Ara-C.

In another experiment, femoral bone marrow enriched for early hematopoietic progenitors were taken from Balb/c mice 4 days after receiving a single intravenous injection of 5-fluorouracil (5-FU) at 150 mg/kg body weight. Harvested bone marrow cells (BM) at $3.75 \times 10^5$ cells in 1 ml were incubated in culture media consisting of Iscove's modified Dulbecco's medium with 20% fetal bovine serum (FBS) in 24-well cluster plates'supplemented with 100 U/ml purified recombinant human IL-1β and 20 ng/ml purified recombinant murine kit ligand (mKL, Muench et al., 1992). At the end of the fourth day in liquid culture, TGF-β3 was added at the indicated concentration (0.001 ng/ml to 100 ng/ml final concentration) and further incubated for an additional fourteen hours at 37° C. in a fully humidified 5% $CO^2$ atmosphere. Following the fourteen hour incubation with TGF-β3, Ara-C at a final concentration of 100 μg/ml was added and incubated for an additional 28 hours at 37° C. in a fully humidified 5% $CO^2$ atmosphere. At the end of the incubation, the various treated BM was diluted once (1:10) and washed three times by centrifugation with chilled Dulbecco's phosphate buffered saline containing 10% FBS at 4° C. Colony forming cells were assayed using a double-layer agarose'system. Sixty-millimeter petri dishes containing a 2-ml underlayer consisting of culture media, cytokines and 0.5% agarose were overlayed with 1 ml of treated and washed BM cells suspended in culture media containing 0.36% agarose. The final concentration of cytokines in the double-layer was 10% WEHI-3-conditioned medium 1 (as a source of murine IL-3), 100 U/ml IL-1β and 1000 U/ml rmGM-CSF. The cell concentration in the 1 ml of cell layer was $4 \times 10^4$ cells treated. Double layer cultures were incubated for 10 days at 37° C. under low oxygen tension (5%$O_2$/5%$CO^2$/90%$N_2$). Each 60 mm plate was either fixed with 2 ml of 0.5% glutaraldehyde in PBS or stained with 2 ml of a solution of iodonitrotetrazolium (INT) (1 mg/ml) and scored for colony formation. FIG. 16 demonstrates Transforming Growth Factor Beta concentration dependent chemoprotection of the early hematopoietic stem cells from the cytotoxic effects of chemotherapeutic agents (i.e. Ara-C). There is a significantly greater number of HPP cells and total colony forming cells when pretreated with >0.01 ng/ml TGF-β3 relative to the control cells exposed to Ara-C without TGF-β3. At and above 1 ng/ml TGF-β3 shows similar levels of chemoprotection by TGF-β3. There does not appear to be less chemoprotection when higher concentrations of TGF-β3 are used.

Similar ex vivo hematopoietic chemoprotection experiments are performed using TGF-β1, TGF-β2, TGF-β4, and TGF-β5.

EXAMPLE 15

Transforming Growth Factor Beta for Protection of Lung Tissue

TGF-β3 is used as a radioprotectant and chemoprotectant of normal lung tissue. Radiation induced and chemotherapy induced pulmonary cytotoxicity is reduced by administration of any one of the following TGF-βs: TGF-β1, TGF-β2, TGF-β3, TGF-β4 or TGF-β5. The TGF-β is preferably administered by inhalation (e.g. of a vapor, mist or aerosol), but systemic delivery is also effective. TGF-β is preferably administered prior to chemotherapy or radiotherapy. TGF-β prevents cytotoxic poisoning of normal lung epithelial cells and normal lung endothelial cells.

TABLE A (Additional chemotherapeutic drugs)
Gilman et al., 1990

| | |
|---|---|
| 2-Ethylhydrazide | Cisplatin (cis-DDP) |
| 2,2',2"-Trichlorotri- | Cyclophosphamide |
| ethylamine | Cytarabine (cytosine |
| 6-Diazo-5-oxo-L-norleucine | arabinoside; Ara-C) |
| Aceglatone | Dacarbazine (DTIC; |
| Aclacinomycins | dimethyltriazenoimid- |
| Actinomycin $F_1$ | azolecarboxamide) |
| Aminoglutethimide | Dactinomycin (actino- |
| Amsacrine | mycin D) |
| Ancitabine | Daunorubicin (daunomycin; |
| Anthramycin | rubidomycin) |
| Azacitidine | Defosfamide |
| Azaserine | Demecolcine |
| Benzodepa | Denopterin |
| Bestrabucil | Diaziquone |
| Bisantrene | Diethylstilbestrol |
| Bleomycin | Doxifluridine |
| Buserelin | Doxorubicin |
| Busulfan | Dromostanolone Propionate |
| Cactinomycin | Eflornithine |
| Calusterone | Elliptinium Acetate |
| Carboplatin | Enocitabine |
| Carboquone | Epirubicin |
| Carmofur | Epitiostanol |
| Carmustine (BCNU) | Estramustine |
| Carubicin | Ethinyl estradiol |
| Chlorambucil | Etoglucid |
| Chlormadinone Acetate | Etoposide |
| Chlornaphazine | Floxuridine |
| Chlorozotocin | (fluorodeoxyuridine; |
| Chromomycins | Fudr) |
| Fludarabine | mercaptopurine; 6-MP) |
| Fluorouracil (5- | Methotrexate (amethopterin) |
| fluororuracil; 5-FU) | Meturedepa |
| Fluoxymesterone | Mitguazone |
| Flutamide | Mitobronitol |
| Fosfestrol | Mitolactol |
| Fotemusine | Mitomycin (mitomycin C) |
| Gallium Nitrate | Mitotane (o,p'-DDD) |
| Goserelin | Mitoxantrone |
| Hexamethylmelamine | Mopidamol |
| Hexestrol | Mycophenolic Acid |
| Hydroxyprogesterone caproate | Nilutamide |
| Hydroxyurea | Nimustine |
| Ifosfamide | Nitracrine |
| Improsulfan | Nogalamycin |
| Interferon alfa | Novembichin |
| Interferon-gamma | Olivomycins |
| Interferon-β | Pentostatin (2'- |
| Interleukin-2 | deoxycoformycin) |

TABLE A-continued (Additional chemotherapeutic drugs)
Gilman et al., 1990

| | |
|---|---|
| L-Asparaginase | Peplomycin |
| Lentinan | Phenamet |
| Leuprolide | Phenesterine |
| Leuprolide | Pipobroman |
| Lomustine (CCNU) | Piposulfan |
| Lonidamine | Pirarubicin |
| Mannomustine | Plicamycin (mithramycin) |
| Mechlorethamine ($HN_2$) | Podophyllinic Acid |
| Mechlorethamine Oxide | Polyestradiol Phosphate |
| Hydrochloride | Porfiromycin |
| Medroxyprogesterone acetate | Prednimustine |
| Megestrol acetate | Prednisone |
| Melengestrol | Procarbazine (N- |
| Melphalan (L-sarcolysin) | methylhydrazine, MIH) |
| Mepitiostane | PSK ® (KRESTIN) |
| Mercaptopurine (6- | Pteropterin |
| Puromycin | Vincristine |
| Ranimustine | Vindesine |
| Razoxane | Zinostatin |
| Semustine (methyl-CCNU) | Zorubicin |
| Sizofiran | |
| Spirogermanium | |
| Streptonigrin | |
| Streptozocin | |
| (streptozotocin) | |
| Tamoxifen | |
| Taxol | |
| Teniposide | |
| Tenuazonic Acid | |
| Testolactone | |
| Testosterone propionate | |
| Thiamiprine | |
| Thioguanine (6-thioguanine; | |
| TG) | |
| Thiotepa | |
| Toremifene | |
| Traziquone | |
| Triethylenemelamine | |
| Triethylenephosphoramide | |
| Trilostane | |
| Trimethylolmelamine | |
| Trimetrexate | |
| Triptorelin | |
| Trofosfamide | |
| Tubercidin | |
| Ubenimex | |
| Uracil Mustard | |
| Uredepa | |
| Urethan | |
| Vinblastine (VLB) | |

REFERENCES

1. Assoian et al. (1983) *J. Biol. Chem*, 258: 7155
2. Brunner et al. (1988) *Mol. Cell. Biol*. 8(5):2229.
3. Cashman, J. D. et al. (1990) *Blood*, 75:96.
4. Centrella, et al. (1987) *J. Biol. Chem*, 262:2869.
5. Centrella, et al. (1986) *Endocrinol*. 119:2306.
6. Cerletti, N. et al., European Patent Publication No. 0 433,225 A1, published Jun. 19, 1991.
7. Derynck. R. et al., U.S. Pat. No. 4,886,747, issued Dec. 12, 1990.
8. Eisen, D. et al. (1990) *J. Amer. Acad. of Dermatology* 23:1259–1264.
9. Gesme (1992) *Contemporary Oncoloay* 2:35.
10. Gilman, A. G. et al., Eds. (1990) *The Pharmacological Basis of Therapeutics*, 8th Ed., pp. 1205–1207, Pergamon Press, New York.
11. Goey, H. et al.(1989) *J. Immunol*. 143:877–880.
12. Golde, D. W. et al. (1980) *Proc. Natl. Acad. Sci.* USA 77, 593–597.

13. Guggenheimer, J. et al. (1977) *Oral Sura. Med. Oral Pathol.*, 44:58–63.
14. Hornung and Longo (1992) *Blood* 80: 77–83
15. Iwata, K. K. et al. (1985) *Cancer Res.* 45:2689–2694.
16. Iwata, K. K., et al., (1992 A) International Publication No. WO 92/00318, published Jan. 9, 1992.
17. Iwata, K. K., et al., (1992 B) International Publication No. WO 92/00330, published Jan. 9, 1992.
18. Lockhart, O. B. and Sonis, S. T. (1981) *J. Dermatol Surg.* 7:1019–25.
19. Madisen, L. et al. (1989) *DNA* 8:205–212.
20. Madisen et al. (1988) *J. Cell Biochem. Suppl.* pp 199.
21. McMaster et al. EP 542 679 Novel Hybrid Transforming Growth Factors
22. Moore, M. A. S. et al. (1987) *PNAS* 84:7134–7138.
23. Mossman, T. (1983) *J. Immuno. Methods* 65:55–65.
24. Moyer, M. et al. (1990) In *Colon Cancer Cells*. M. Moyer and G. Poste, Eds. pp.85–136, Academic Press, New York.
25. Muench, M. O. et al. (1992). *Exp. Hematol.* 20:339–349.
26. Nilsson, B. et al. (1988) In: *Advances in Gene Technology: Protein Engineering and Production*. K. Brew et al., Eds., IRL Press, Washington, D.C.:pp. 122–123.
27. Ogawa, Y. et al., (1992) *J. Biol. Chem.* 267:2325.
28. Perlman and Halvorson (1983) *J. Mol. Biol.* 107:391–409.
29. Pincher et al. (1985) *Biochem. Biophys. Res. Commun.*, 133(3):1026.
30. Posner, M. R. (1990) *J. Natl. Cancer Inst.* 82(21):1710–1714.
31. Potten, C. S. (1990) Int. Radiat. Biol. 58:925–973
32. Potten, C. S. (1991) in *Chemically Induced Cell Proliferation*, Wiley-Liss, Inc., p.155–171
33. Purchio, A. F., et al., UK Patent Publication No. GB-2210620A, published Jun. 14, 1990
34. Shamsuddin, A. M. (1990) In: *Colon Cancer Cells*. M. Moyer and G. Poste, Eds., pp 137–153, Academic Press, New York.
35. Shieh, J.-H., Peterson, R. H. F., and Moore, M. A. S. (1991). *J. Immunol.* 147:2984–2990.
36. Sonis, S. et al. (1978) JADA, 97:468–472.
37. Sonis, A. and Sonis, S. (1979) *Journal of Pedodontics* Winter:122–128.
38. Sonis, S. et al. (1988) *Oral Surg.* 65:19–22.
39. Sonis, S. et al. (1990) *Oral Surg. Oral Med. Oral Pathol.* 69:437–443.
40. Sonis, S., (1990) In: *Cancer Principles and Practice or Oncology*. Ed. devita, V.; Hellman, S.; Rosenberg, S. J. Volume 2, 3rd Edition. J. B. Lippincott Company, Philadelphia.
41. Stover, D. E., (1990) In: *Cancer Principles and Practice or Oncology*. Ed. devita, V.; Hellman, S.; Rosenberg, S. J. Volume 2, 3rd Edition. J. B. Lippincott Company, Philadelphia.
42. Sonis, S., and Clark, J. (1991) *Oncology*, 5(12):11–17.
43. Strife, A. et al. (1988). *Cancer Res.* 48, 1035–1041.
44. Strife, A. (1987) *Blood* 69:1508–1523.
45. ten Dijke, P. et al, (1990 A) International Publication No. WO 90/14360, published Nov. 29, 1990.
46. ten Dijke, P., et al., (1990 B) *Annals of New York Academy*, pp. 26–42.
47. Twardzik et al. (1989) *J. Natl. Cancer Inst.* 81(15):1182.
48. Wong, et al (1975) *Proc. Natl. Acad. Sci.* USA 72:3167–3171.
49. Wrann, M. et al. (1987) *EMBO J.* 6: 1633–1636.

What is claimed is:

1. A method for inhibiting cytotoxic poisoning of normal cells in a subject which comprises administering to the subject an amount of a Transforming Growth Factor Beta 3 effective to slow the growth of normal cells and thereby inhibit the cytotoxic poisoning of the normal cells in the subject.

2. A method of claim 1, wherein the normal cells are hematopoietic progenitor cells.

3. A method of claim 1, wherein the Transforming Growth Factor Beta 3 is a recombinant TGF-β3.

4. A method of claim 1, wherein the administration is initiated prior to anti-neoplastic therapy for the subject.

5. A method of claim 4, wherein the anti-neoplastic therapy is chemotherapy.

6. A method of claim 4, wherein the anti-neoplastic therapy is radiation therapy.

7. A method of claim 1, wherein the subject is a pediatric subject.

8. A method of claim 1, wherein the administration is topical.

9. A method of claim 8, wherein the topically administered amount is between 1 ng and 10 mg.

10. A method of claim 1, wherein the administration is systemic.

11. A method of claim 10, wherein the systemically administered amount is between 1 ng/kg body weight/day and 500 μg/kg body weight/day.

12. The method of claim 1, wherein the normal cells are epithelial cells.

13. The method of claim 1, wherein the epithelial cells are esophageal tract epithelial cells.

14. The method of claim 12, wherein the epithelial cells are oral epithelial cells.

15. The method of claim 12, wherein the epithelial cells are gastrointestinal epithelial cells.

16. The method of claim 15, wherein the gastrointestinal epithelial cells are colon crypt stem cells.

17. The method of claim 15, wherein the gastrointestinal epithelial cells are enterocytic cells.

18. The method of claim 12, wherein the epithelial cells are follicle epithelial cells.

19. The method of claim 1, wherein the normal cells are stem cells.

20. The method of claim 19, wherein the subject is receiving anti-neoplastic therapy and a cytokine is used in conjunction with anti-neoplastic therapy and the stem cells are hematopoietic stem cells.

21. The method of claim 4, wherein a mitogen is contacted with the cells following anti-neoplastic therapy.

22. The method of claim 21, wherein the mitogen is EGF.

23. The method of claim 21, wherein the mitogen is TGF-α.

24. The method of claim 21, wherein the mitogen is amphiregulin, FGF, IGF-1, or a combination thereof.

25. The method of claim 21, wherein the mitogen is an epithelial cell mitogen or a hematopoietic cell mitogen.

26. The method of claim 19, wherein a cytokine is used following anti-neoplastic therapy.

27. The method of claim 26, wherein the cytokine is G-CSF.

28. The method of claim 26, wherein the cytokine is GM-CSF.

29. The method of claim 26, wherein the cytokine is IL-3.

30. The method of claim 26, wherein the cytokine is IL-3.

31. The method of claim 26, wherein the cytokine is kit ligand.

32. The method of claim 26, wherein the cytokine is IL-6.

* * * * *